(12) United States Patent
Lewis

(10) Patent No.: US 6,170,318 B1
(45) Date of Patent: Jan. 9, 2001

(54) METHODS OF USE FOR SENSOR BASED FLUID DETECTION DEVICES

(75) Inventor: Nathan S. Lewis, La Canada, CA (US)

(73) Assignee: California Institute of Technology, Pasadena, CA (US)

(*) Notice: Under 35 U.S.C. 154(b), the term of this patent shall be extended for 0 days.

(21) Appl. No.: 09/183,724

(22) Filed: Oct. 30, 1998

Related U.S. Application Data

(63) Continuation-in-part of application No. 08/986,500, filed on Dec. 8, 1997, now Pat. No. 6,010,616, which is a continuation of application No. 08/689,227, filed on Aug. 7, 1996, now Pat. No. 5,698,089, which is a continuation of application No. 08/410,809, filed on Mar. 27, 1995, now Pat. No. 5,571,401.

(51) Int. Cl.[7] .................. G01N 33/497; G01N 27/00; G08B 17/10

(52) U.S. Cl. .................. 73/23.34; 422/98; 340/632

(58) Field of Search .................. 73/23.34, 23.2, 73/31.06, 31.05; 422/90, 98, 82.02; 340/632, 634; 205/787

(56) References Cited

U.S. PATENT DOCUMENTS

| 3,045,198 | 7/1962 | Dolan et al. . |
| 3,428,892 | 2/1969 | Meinhard . |
| 3,970,863 | 7/1976 | Kishikawa et al. . |
| 3,999,122 | 12/1976 | Winstel et al. . |

(List continued on next page.)

FOREIGN PATENT DOCUMENTS

| 286 307 | 10/1988 | (EP) . |
| 293 255 | 11/1988 | (EP) . |
| 298 463 | 1/1989 | (EP) . |

(List continued on next page.)

OTHER PUBLICATIONS

Corcoran et al., "Integrated tin oxide sensors of low power consumption for use in gas and odour sensing," *Sensors and Actuators B*, 15–16:32–37 (1993).*

DeVries, et al., "Synaptic circuitry of the retina and olfactory bulb," *Cell/Neuron*, 72/10 (Suppl):139–149 (1993).*

(List continued on next page.)

*Primary Examiner*—Hezron Williams
*Assistant Examiner*—Jay L. Politzer
(74) *Attorney, Agent, or Firm*—Townsend and Townsend and Crew LLP

(57) ABSTRACT

Methods of use and devices for detecting analyte in fluid. A system for detecting an analyte in a fluid is described comprising a substrate having a sensor comprising a first organic material and a second organic material where the sensor has a response to permeation by an analyte. A detector is operatively associated with the sensor. Further, a fluid delivery appliance is operatively associated with the sensor. The sensor device has information storage and processing equipment, which is operably connected with the device. This device compares a response from the detector with a stored ideal response to detect the presence of analyte. An integrated system for detecting an analyte in a fluid is also described where the sensing device, detector, information storage and processing device, and fluid delivery device are incorporated in a substrate. Methods for use for the above system are also described where the first organic material and a second organic material are sensed and the analyte is detected with a detector operatively associated with the sensor. The method provides for a device, which delivers fluid to the sensor and measures the response of the sensor with the detector. Further, the response is compared to a stored ideal response for the analyte to determine the presence of the analyte. In different embodiments, the fluid measured may be a gaseous fluid, a liquid, or a fluid extracted from a solid. Methods of fluid delivery for each embodiment are accordingly provided.

19 Claims, 32 Drawing Sheets

U.S. PATENT DOCUMENTS

| | | | |
|---|---|---|---|
| 4,636,767 | * 1/1987 | Barger et al. | 338/34 |
| 4,674,320 | 6/1987 | Hirchfeld . | |
| 4,759,210 | 7/1988 | Wohltjen . | |
| 4,795,968 | 1/1989 | Madou et al. . | |
| 4,812,221 | 3/1989 | Madou et al. . | |
| 4,847,783 | 7/1989 | Grace et al. . | |
| 4,855,706 | 8/1989 | Hauptly . | |
| 4,884,435 | 12/1989 | Ehara . | |
| 4,142,400 | 3/1979 | Colla et al. . | |
| 4,225,410 | 9/1980 | Pace . | |
| 4,236,307 | 12/1980 | Colla et al. . | |
| 4,322,383 | 3/1982 | Yasuda et al. . | |
| 4,457,161 | 7/1984 | Iwanaga et al. . | |
| 4,542,640 | 9/1985 | Clifford . | |
| 4,631,952 | 12/1986 | Donaghey . | |
| 4,893,180 | 1/1990 | Kolesar, Jr. . | |
| 4,900,405 | 2/1990 | Otagawa et al. . | |
| 4,907,441 | 3/1990 | Shurmer . | |
| 4,911,892 | 3/1990 | Grace et al. . | |
| 4,926,156 | 5/1990 | Dickert et al. . | |
| 4,992,244 | * 2/1991 | Grate | 422/98 |
| 5,023,133 | 6/1991 | Yodice et al. . | |
| 5,034,192 | * 7/1991 | Wrighton et al. | 422/82.02 |
| 5,045,285 | 9/1991 | Kolesar, Jr. . | |
| 5,079,944 | 1/1992 | Boenning et al. . | |
| 5,089,780 | 2/1992 | Megerle . | |
| 5,120,421 | 6/1992 | Glass et al. . | |
| 5,137,991 | 8/1992 | Epstein et al. . | |
| 5,145,645 | 9/1992 | Zakin et al. . | |
| 5,150,603 | 9/1992 | Boenning et al. . | |
| 5,177,994 | 1/1993 | Moriizumi et al. . | |
| 5,217,692 | 6/1993 | Rump et al. . | |
| 5,239,483 | 8/1993 | Weir . | |
| 5,256,574 | 10/1993 | Neuburger et al. . | |
| 5,571,401 | * 11/1996 | Lewis et al. | 205/787 |
| 5,698,089 | * 12/1997 | Lewis et al. | 205/787 |
| 5,756,879 | * 5/1998 | Yamagishi et al. | 73/28.01 |
| 5,788,833 | * 8/1998 | Lewis et al. | 205/787 |
| 5,807,701 | * 9/1998 | Payne et al. | 435/34 |
| 5,891,398 | * 4/1999 | Lewis et al. | 422/82.02 |
| 5,911,872 | * 6/1999 | Lewis et al. | 205/787 |
| 5,945,069 | * 8/1999 | Buehler | 422/90 |
| 5,951,846 | * 9/1999 | Lewis et al. | 205/787 |
| 5,959,191 | * 9/1999 | Lewis et al. | 73/31.05 |
| 6,010,616 | * 1/2000 | Lewis et al. | 205/787 |
| 6,013,229 | * 1/2000 | Lewis et al. | 422/82.02 |
| 6,017,440 | * 1/2000 | Lewis et al. | 205/777.5 |

FOREIGN PATENT DOCUMENTS

| | | | |
|---|---|---|---|
| 1 041 575 | 9/1966 | (GB) . | |
| 2 203 249 | 10/1988 | (GB) . | |
| WO93/03355 | * 2/1993 | (GB) | G01N/27/12 |
| WO 85/01351 | 3/1985 | (WO) . | |
| WO 93/06237 | 4/1993 | (WO) . | |
| WO 96/07901A1 | 3/1996 | (WO) . | |
| WO 96/30750 | 10/1996 | (WO) . | |

OTHER PUBLICATIONS

Diaz, et al., "Electrooxidation of aromatic oligomers and conducting polymers," *J. Elect. Chem.*, 121:355–361 (1981).*

Gardner, et al., "Integrated array sensor for detecting organic solvents," *Sensors and Actuators B*, 26–27 (1995).*

Gardner, J.W., et al., "A brief history of electronic noses," *Sensors and Actuators B*, 18–19:221–220 (1994).*

Gardner, J.W., et al., "A multisensor system for beer flavour monitoring using an array of conducting polymers and predictive classifiers," *Sensors and Actuators B*, 18–19:240–243 (1994).*

Gardner, J.W., et al., "Application of an electronic nose to the discrimination of coffees," *Sensors and Actuators B*, 6:71–75 (1992).*

Gardner, J.W., et al., "Design of conducting polymer gas sensors: Modeling and experiment," *Synthetic Metals*, 55–57:3665–3670 (1993).*

Gardner, J.W., et al., "Detection of vapours and odours from a multisensor array using pattern recognition. Part 1. Principal component and cluster analysis," *Sensors and Actuators B*, 4:109–115 (1991).*

Gardner, J.W., et al., "Detection of vapours and odours from a multisensor array using pattern–recognition techniques. Part 2. Artificial neural networks," *Sensors and Actuators B*, 9:9–15 (1992).*

Gardner, J.W., et al., "Integrated tin oxide odour sensor," *Sensors and Actuators B*, 4:117–121 (1991).*

Grate, J.W., et al., "Smart sensor system for trace organophosphorus and organosulfur vapor detection employing a temperature–controlled array of surface acoustic wave sensors, automated sample preconcentration, and pattern recognition," *Anal. Chem.*, 65:1868–1881 (1993).*

Grate, J.W., et al., "Solubility interactions and the design of chemically selective sorbent coatings for chemical sensors and arrays," *Sensors and Actuators B*, 3:85–111 (1991).*

Greenfield, Philip, "AromaScan sniffs out medical applications", *Clinica*, 804:20–21, May 1994.*

Kanazawa, et al., "Electrical properties of pyrrole and its copolymers," *Synthetic Metals*, 4:119–130 (1981).*

Kauer, "Contributions of topography and parallel processing to odor coding in the vertebrate olfactory pathway," *TINS*, 14(2):79–85 (1991).*

Kaufman, et al., "Evolution of polaron states into bipolarons in polypyrrole," *Physical Review Letters*, 53(19):1005–1008 (1984).*

Lancet, et al., "Olfactory receptors," *Current Biology*, 3(10):668–674 (1993).*

Lundberg et al., "Resistivity of a composite conducting polymer as a function of temperature, pressure and environment: Applications as a pressure and gas concentrator," *J. Appl. Phys.*, 60(3), Aug. 1986,*

Lundström, I., et al., "Artificial 'olfactory' images from a chemical sensor using a light–pulse technique," *Nature*, 352:47–50 (1991).*

Morris, et al., "The system ethanol–methanol at 40oC," *Canadian J. Res.*, 20(B):207–211 (1942).*

Musio, et al., "High–frequency a.c. investigation of conducting polymer gas sensors," *Sensors and Actuators B*, 223–226 (1995).*

Pearce, T.C., et al., "Electronic nose for monitoring the flavour of beers," *Analyst*, 118:371–377 (1993).*

Reed, "Signaling pathways on odorant detection," *Neuron*, 8:205–209 (1992).*

Salmon, et al., "A chemical route to pyrrole polymer films," *J. Polymer Sci.*, 20(3):187–193 (1982).*

Stetter, et al., "Sensor array and catalytic filament for chemical analysis of vapors and mixtures," *Sensors and Actuators*, B1:43–47 (1990).*

Shurmer, et al., "An electronic nose: a sensitive and discriminating substitute for a mammalian olfactory system," *IEE Proceedings*, 137G(3):197–204 (1990).*

Shurmer, H.V., et al., "Integrated arrays of gas sensors using conducting polymers with molecular sieves," *Sensors and Actuators B*, 4:29–33 (1991).*

* cited by examiner

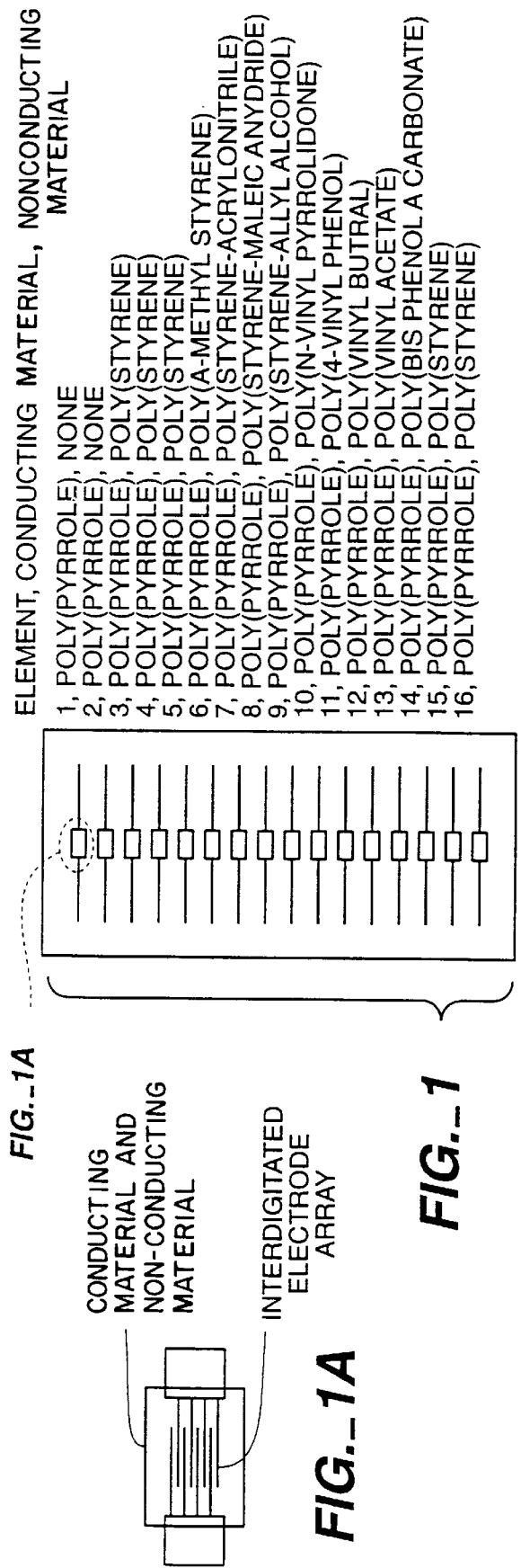
FIG._1A
FIG._1

METHODS OF USE FOR SENSOR BASED FLUID DETECTION DEVICES

This application is a continuation-in-part of U.S. patent application Ser. No. 08/986,500, filed on Dec. 8, 1997, now U.S. Pat. No. 6,010,616, which is a continuation of U.S. patent application Ser. No. 08/689,227, filed on Aug. 7, 1996, now U.S. Pat. No. 5,698,089, which is a continuation of U.S. patent application Ser. No. 08/410,809, filed on Mar. 27, 1995, now U.S. Pat. No. 5,571,401, all of which are incorporated herein by reference in their entireties.

The research carried out in the subject application was carried out in part by grants from the National Science Foundation (CHE 9202583); ARPA (ONR Grant No. N00014-89-J-3198); and was made during the performance of work under a NASA contract and is subject to the provisions of Public Law 96-517 (35 U.S.C. §202).

BACKGROUND OF THE INVENTION

This invention relates generally to sensor systems for detecting analytes in fluids and, more particularly, to sensor systems of this kind that incorporate sensors having electrical resistances that vary according to the presence and concentration of analytes, and to methods of using such sensor systems.

There is considerable interest in developing sensors that act as analogs of the mammalian olfactory system [Lundström et al. Nature 352:47–50 (1991); Shurmer and Gardner, Sens. Act. B 8:1–11 (1992)]. This system is thought to utilize probabilistic repertoires of many different receptors to recognize a single odorant [Reed, Neuron 8:205–209 (1992); Lancet and Ben-Airie, Curr. Biol. 3:668–674 (1993)]. In such a configuration, the burden of recognition is not on highly specific receptors, as in the traditional "lock-and-key" molecular recognition approach to chemical sensing, but lies instead on the distributed pattern processing of the olfactory bulb and the brain [Kauer, TINS 14:79–85 (1991); DeVries and Baylor, Cell 10(S):139–149 (1993)].

Prior attempts to produce a broadly responsive sensor array have exploited heated metal oxide thin film resistors [Gardner et al., Sens. Act. B 4:117–121 (1991); Gardner et al., Sens. Act. B 6:71–75 (1991); Corcoran et al., Sens. Act. B 15:32–37 (1993)], polymer sorption layers on the surfaces of acoustic wave resonators [Grate and Abraham, Sens. Act. B 3:85–111 (1991); Grate et al. Anal. Chem. 65:1868–1881 (1993)], arrays of electrochemical detectors [Stetter et al., Anal. Chem. 58:860–866 (1986); Stetter et al., Sens. Act. B 1:43–47 (1990); Stetter et al., Anal. Chem. Acta 284:1–11 (1993)], or conductive polymers [Pearce et al., Analyst 118:371–377 (1993); Shurmer et al., Sens. Act. B 4:29–33 (1991)]. Arrays of metal oxide thin film resistors, typically based on tin oxide ($SnO_2$) films that have been coated with various catalysts, yield distinct, diagnostic responses for several vapors [Gardner et al., Sens. Act. B 4:117–121 (1991); Gardner et al., Sens. Act. B 6:71–75 (1991); Corcoran et al., Sens. Act. B 15:32–37 (1993)]. However, due to the lack of understanding of catalyst function, $SnO_2$ arrays do not allow deliberate chemical control of the response of elements in the arrays nor reproducibility of response from array to array.

Metal oxide sensors such as $SnO_2$ films that have been coated with various catalysts are used primarily to detect gas leaks, e.g., carbon monoxide (CO). Gas leak detection is a specific chemical sensing application in which the existing technology is well-established. The current technology in this area is problematic in that metal oxide sensors work only at high power, i.e., they must be plugged into a conventional ac power source. This is because the metal oxide element must be heated for the chemical detection to work. The heated element literally burns methane, propane, CO, etc., to carbon dioxide. Oxygen for the combustion reaction is actually supplied by the metal oxide itself, and it is the absence of oxygen that sets off an electrical current in the metal oxide element thereby detecting the presence of the gas. Different gases are detected by metal oxide sensors based upon the addition of certain catalysts.

Existing metal oxide sensors are single-channel devices that collect information from a single sensor and that are thus designed to trigger only when the gas, e.g., CO, is present. However, the devices can be prone to false alarms, and in many cases consumers disable the devices because of this annoyance. A sensor is needed with a lower false alarm rate to overcome the problematic user error. This can be accomplished by adding an additional sensor to CO detectors, which provides information that the odor is not CO, thereby lowering the occurrence of false alarms and providing significant product improvement.

Also, profiling a chemical environment, rather than simply indicating the presence or absence of a gas leak, has far more utility in many applications, e.g., fire-fighting. A hand-held or chip-based product that could identify the chemicals given off by fires could be used by fire fighters to indicate the particular fire retardants that would work best and the protective gear to wear, etc. Such 'smart' environmental profilers would be suitable for integration into standard room monitoring devices, e.g., thermostats, smoke detectors, etc., and thereby represent a major market opportunity.

Surface acoustic wave resonators are extremely sensitive to both mass and acoustic impedance changes of the coatings in array elements, but the signal transduction mechanism involves somewhat complicated electronics, requiring frequency measurement to 1 Hz while sustaining a 100 MHz Rayleigh wave in the crystal [Grate and Abraham, Sens. Act. B 3:85–111 (1991); Grate et al. Anal. Chem. 65:1868–1881 (1993)]. Attempts have been made to construct sensors with conducting polymer elements that have been grown electrochemically through nominally identical polymer films and coatings [Pearce et al., Analyst 118:371–377 (1993); Shurmer et al., Sens. Act. B 4:29–33 (1991); Topart and Josowicz, J. Phys. Chem. 96:7824–7830 (1992); Charlesworth et al., J. Phys. Chem. 97:5418–5423 (1993)].

Surface acoustic wave resonators are considered problematic in that there is a need to precisely control temperature on each sensor, e.g., to 0.01° C. Also, the sensors generally cannot be manufactured in large numbers, and the complicated technology and complicated circuitry do not allow for chip based sensors.

Electron capture chemical detectors are another example of a well-known chemical sensor technology. The technology is based upon a chemical principle called electron capture, in which electrons are emitted from a filament and captured only by molecules that readily add an electron. These molecules, having added an electron, become negatively charged and can be diverted towards a charged electric plate where they can be detected. A limited number of molecules exhibit this characteristic. These include primarily freons and are the basis for hand-held refrigerant detectors. Freons are responsible for ozone depletion and are considered an environmental hazard. A small chip-based sensor could be useful for detecting freon leaks and could be mounted on refrigeration units for early detection of freon leaks, thus providing near instantaneous detection and mitigation of environmental damage.

Current laboratory-based technology for fluid detection and identification relies heavily on gas chromatography (GC) and mass spectroscopy (MS). These technologies, while important to research and process control and quality control, have their limitations beyond the laboratory setting. Both are confined to bench-top lab analysis and are not suitable for product development outside of research and process control and quality control markets. Often in routine use of GC/MS, one must calibrate the instrumentation based upon what is likely to be in the sample being analyzed. The chemical analysis must be based on a reasonable idea about what is already there, to have confidence in the result of the analysis. A technology is needed that allows odors to be detected in the field, in the office, in the home, or in the industry, in real time. Also, a device is needed that can determine (for a given environment) that unknowns are present requiring further analyses. This is critical in off-odor analysis, such as in quality control, environmental monitoring, and a variety of other applications.

It is therefore an object of the invention to provide a broadly responsive analyte detection sensor array based on a variety of "chemiresistor" elements. Such elements should be simply prepared and are readily modified chemically to respond to a broad range of analytes. In addition, these sensors should yield a rapid, low-power, dc electrical signal in response to the fluid of interest, and their signals should be readily integrated with software- or hardware-based neural networks for purposes of analyte identification.

Further, it is an object of the invention to provide an analyte detection system comprising the sensor, an information storage and processing device, and a fluid delivery appliance. The fluid delivery appliance should be operatively associated with the sensor for delivery of the analyte. No known products, technologies or approaches are capable of generating hand-held general odor detectors. Nor are any known broadly-responsive odor sensors available for many different sensing tasks from the same technology base.

A further object of the invention is to provide a chip-based odor detection system. At present, no known competitive technologies or approaches to odor detection are chip-based. Integration of the sensor, the information storage and processing device, and the fluid delivery system onto a single substrate would provide a significant advancement over existing technology.

II. Relevant Literature

Pearce et al. (1993) *Analyst* 118:371–377 and Gardner et al. (1994) *Sensors and Actuators B* 18–19:240–243 describe polypyrrole-based sensor arrays for monitoring beer flavor. Shurmer (1990) U.S. Pat. No. 4,907,441, describes general sensor arrays with particular electrical circuitry.

SUMMARY OF THE INVENTION

The invention provides methods, apparatus and expert systems for detecting analytes in fluids. The apparatus include a chemical sensor comprising first and second conductive elements (e.g., electrical leads) electrically coupled to a chemically sensitive resistor, which provides an electrical path between the conductive elements. The resistor comprises a plurality of alternating nonconductive regions (comprising a nonconductive organic polymer) and conductive regions (comprising a conductive material). The electrical path between the first and second conductive elements is transverse to (i.e., passes through) said plurality of alternating nonconductive and conductive regions. In use, the resistor provides a difference in resistance between the conductive elements when contacted with a fluid comprising a chemical analyte at a first concentration, than when contacted with a fluid comprising the chemical analyte at a second different concentration.

One embodiment of the invention is a system for detecting an analyte in a fluid includes a substrate having a sensor comprising a conductive organic material and a nonconductive organic material, the sensor having a response to permeation by an analyte and a detector operatively associated with the sensor; and a fluid delivery appliance, whereby fluid can be delivered to the sensor. In certain embodiments, an information storage and processing device is operatively connected with the device, for comparing a response from the detector with a stored ideal response, to detect the presence of the analyte. In other embodiments, the information storage and processing device stores ideal responses for two analytes, and the device detects the presence of each analyte.

In another embodiment, an integrated system for detecting an analyte in a fluid includes a sensing device that comprises a substrate and an array of sensors made from a first organic material, having a response to permeation by an analyte, and further comprising a detector operatively associated with the sensor. The sensing device of this embodiment contains an information storage and processing device incorporated in the substrate, for measuring the response profile from the detector. The response profile is compared to the response profile of a stored ideal response for the analyte, to detect the presence of the analyte. The system of this embodiment also contains a fluid delivery mechanism in the substrate, for delivering fluid to the array of sensors.

Methods for using such sensor systems also are described. One preferred method includes the steps of sensing first and second sensors, and detecting the presence of analyte using a detector operatively associated with the sensors. The method also delivers fluid to the sensors and measures the response of the sensors using the detector. Further, the response is compared to a stored ideal response for the analyte, to determine the presence of the analyte. In different embodiments, the fluid measured may be a gaseous fluid, a liquid, or a fluid extracted from a solid. Methods of fluid delivery for each embodiment are accordingly provided.

BRIEF DESCRIPTION OF THE DRAWINGS

FIG. 1 depicts an array of 16 sensors for use in sensing the presence and concentration of unknown analytes, wherein each sensor incorporates a unique formulation of conducting and nonconducting materials.

FIG. 1A is an enlarged view of one sensor of the sensor array of FIG. 1.

FIG. 8A is a schematic representation of a sensor array showing an enlargement of one of the modified ceramic capacitors used as sensing elements. The response patterns generated by the sensor array described in Table 3 are displayed for.

FIG. 10A shows data represented in the first three principle components pc1, pc2 and pc3, while FIG. 10B shows the data when represented in pc 1, pc2, and pc4. A higher degree of discrimination between some solvents could be obtained by considering the fourth principle component as illustrated by larger separations between chloroform, tetrahydrofuran, and isopropyl alcohol in FIG. 10B.

FIG. 26 is a perspective view of a hand held sensor-based fluid detection system used to detect and identify hazardous materials present in landfills and the like.

DESCRIPTION OF THE SPECIFIC EMBODIMENTS

Figure 2:
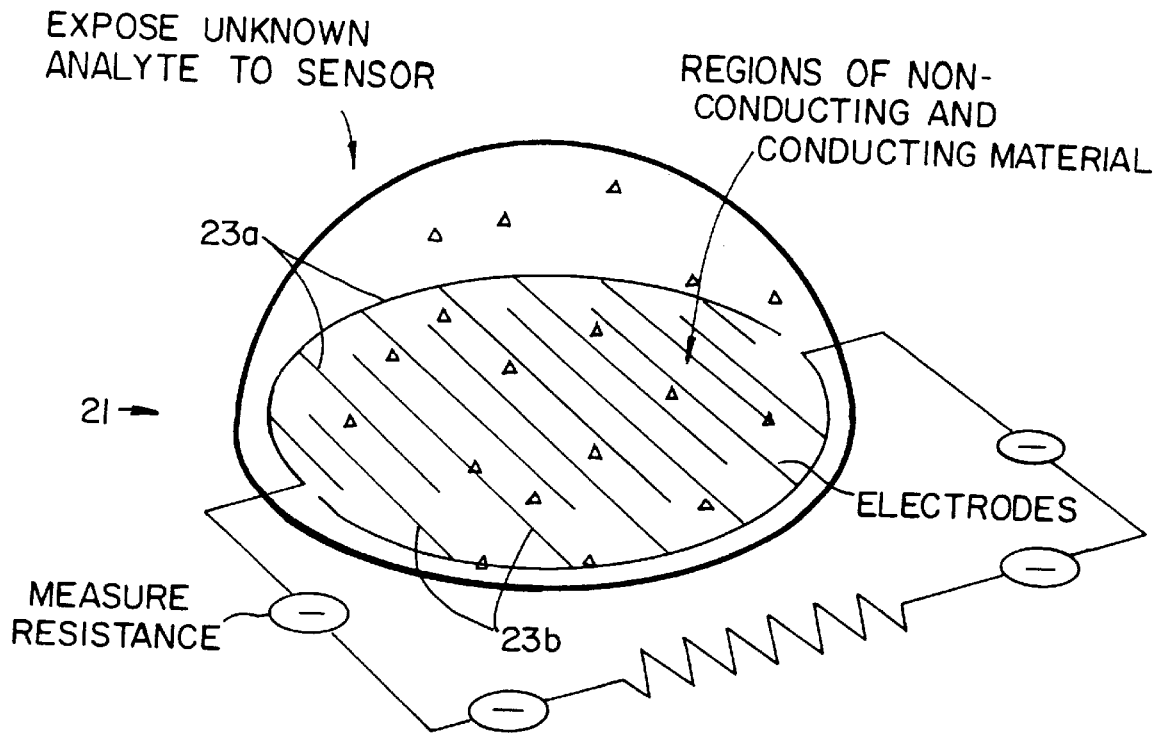
FIG. 2 is a schematic view of one sensor of the sensor array of FIG. 1, depicting the sensor's interdigitized leads and overlaying composite resistive material.
Figure 3:
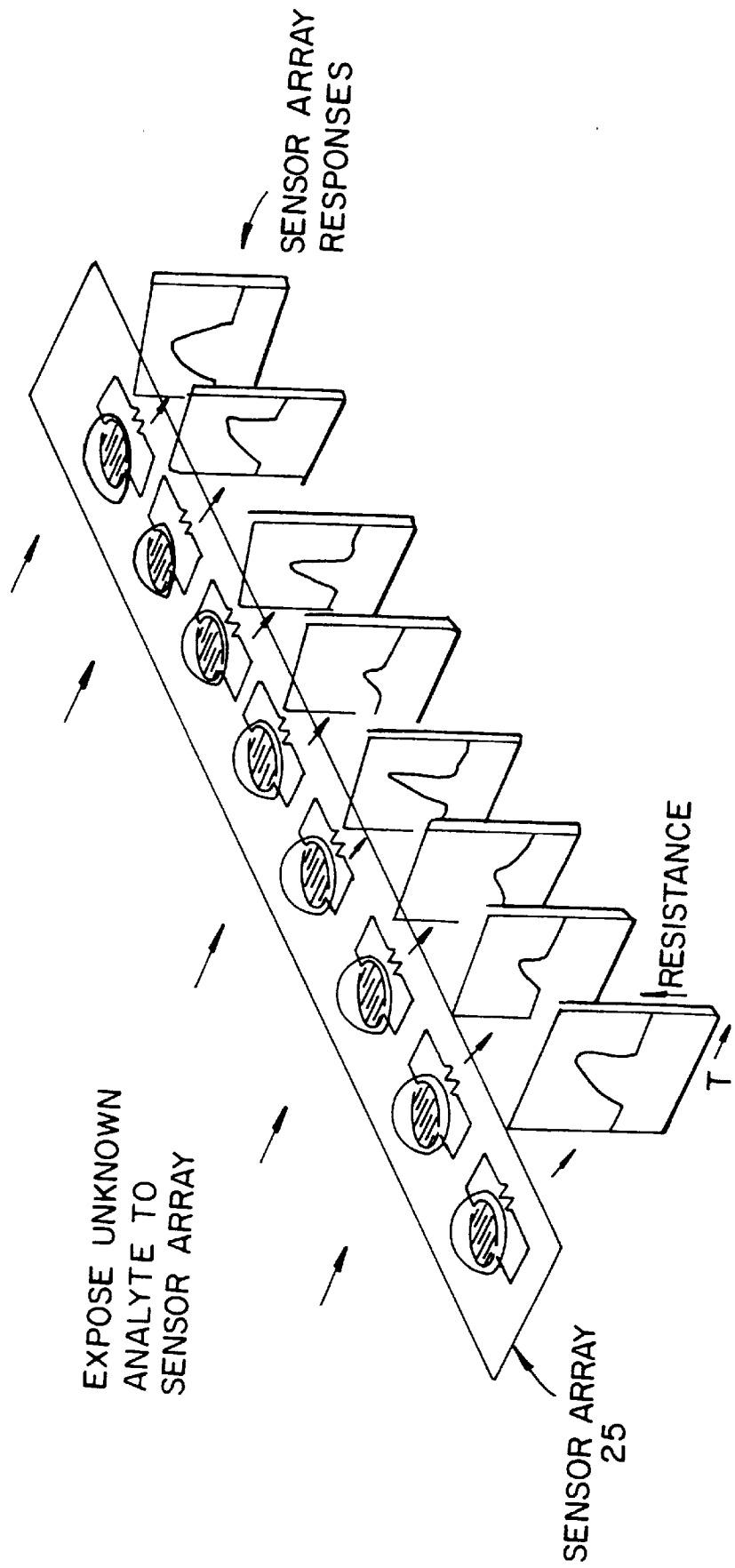
FIG. 3 depicts an array of eight sensors like that of FIG. 2, along with a set of response signals produced by the sensors when exposed to a particular analyte.
Figures 1, 8A:
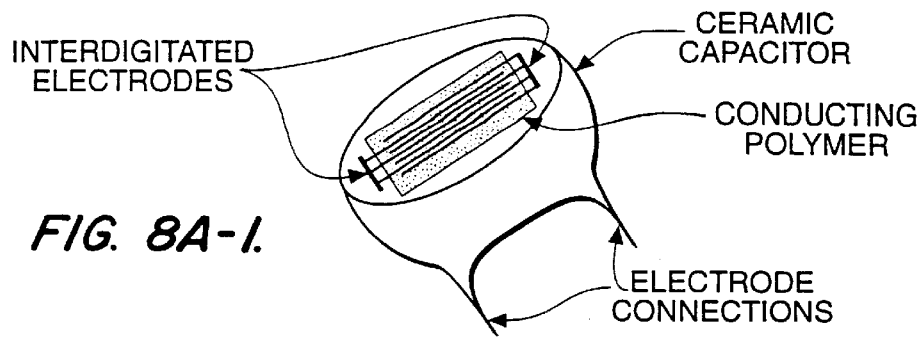
Figure 8A:
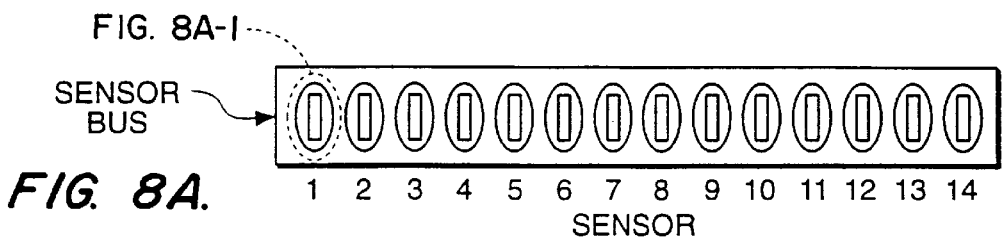
Figure 8B:
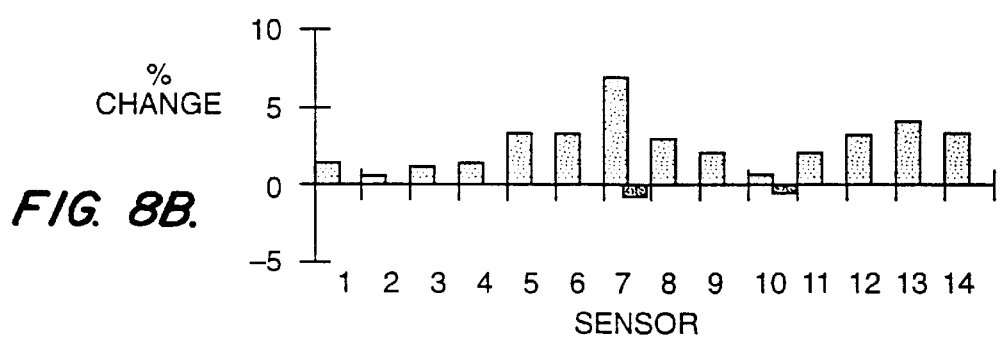
FIG. 8B acetone.
Figure 8C:
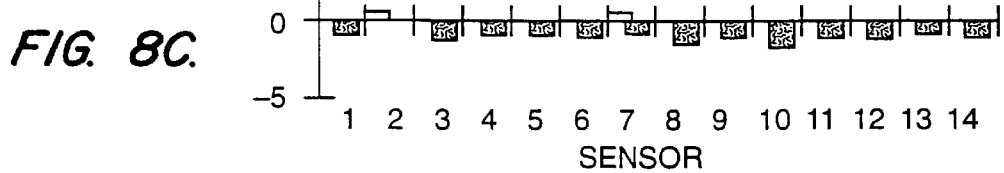
FIG. 8C benzene.
Figure 8D:
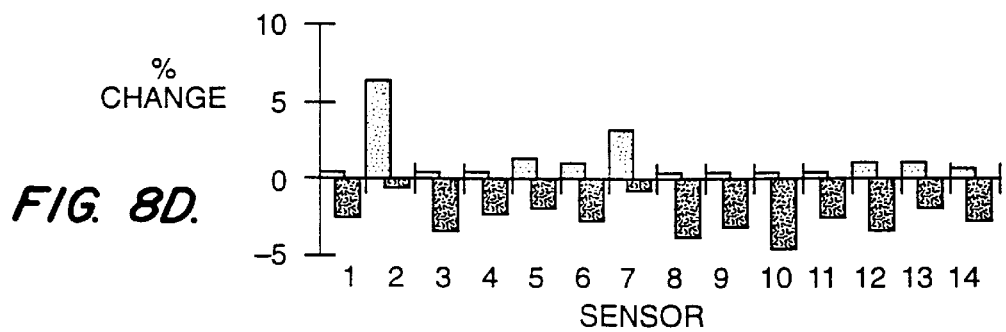
FIG. 8D ethanol.

With reference now to the drawings, and particularly to FIGS. 1–3, there is shown a sensor array for detecting an analyte in a fluid for use in conjunction with an electrical measuring apparatus. The array comprises a plurality of compositionally different chemical sensors, each sensor comprising at least first and second conductive leads electrically coupled to and separated by a chemically sensitive resistor. The leads may be any convenient conductive material, usually a metal, and may be interdigitized to maximize signal-to-noise strength (see FIG. 1A).

The resistor comprises a plurality of alternating nonconductive and conductive regions transverse to the electrical path between the conductive leads. Generally, the resistors are fabricated by blending a conductive material with a nonconductive organic polymer such that the electrically conductive path between the leads coupled to the resistor is interrupted by gaps of non-conductive organic polymer material. For example, in a colloid, suspension or dispersion of particulate conductive material in a matrix of nonconductive organic polymer material, the matrix regions separating the particles provide the gaps. The nonconductive gaps range in path length from about 10 to 1,000 angstroms, usually on the order of 100 angstroms providing individual resistance of about 10 to 1,000 megaohms, usually on the order of 100 megaohms, across each gap. The path length and resistance of a given gap is not constant but rather is believed to change as the nonconductive organic polymer of the region absorbs, adsorbs or imbibes an analyte. Accordingly the dynamic aggregate resistance provided by these gaps in a given resistor is a function of analyte permeation of the nonconductive regions. In some embodiments, the conductive material may also contribute to the dynamic aggregate resistance as a function of analyte permeation (e.g., when the conductive material is a conductive organic polymer such as polypyrrole).

Figure 2A:
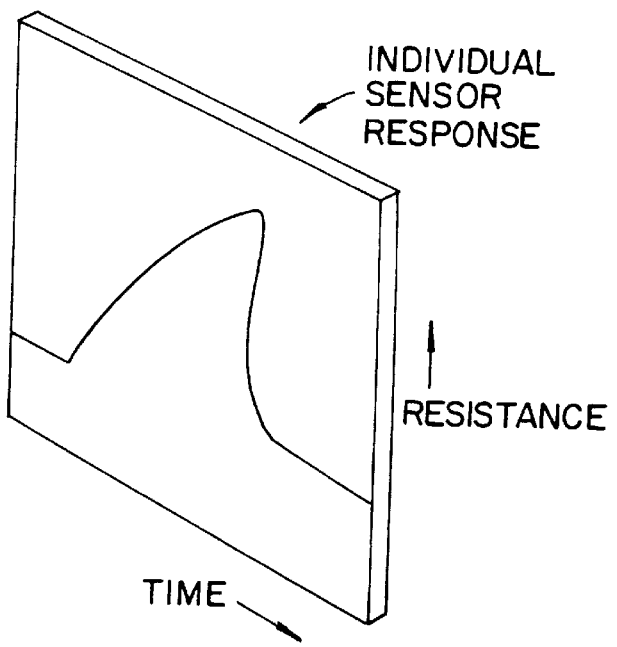
FIG. 2A depicts a typical response signal produced by the sensor of FIG. 2 when exposed to a particular analyte.

FIG. 2 depicts a single sensor 21 having a resistance that varies according to the amount of analyte permeation into the composite polymer material overlaying its interdigitized leads 23a and 23b. Measuring this variable resistance, e.g., by applying a constant voltage to the resistor using an electrical measuring device (not shown), yields a response signal indicative of the nature and concentration of whatever analyte is present. One typical response signal is depicted in FIG. 2A.

Figure 4:
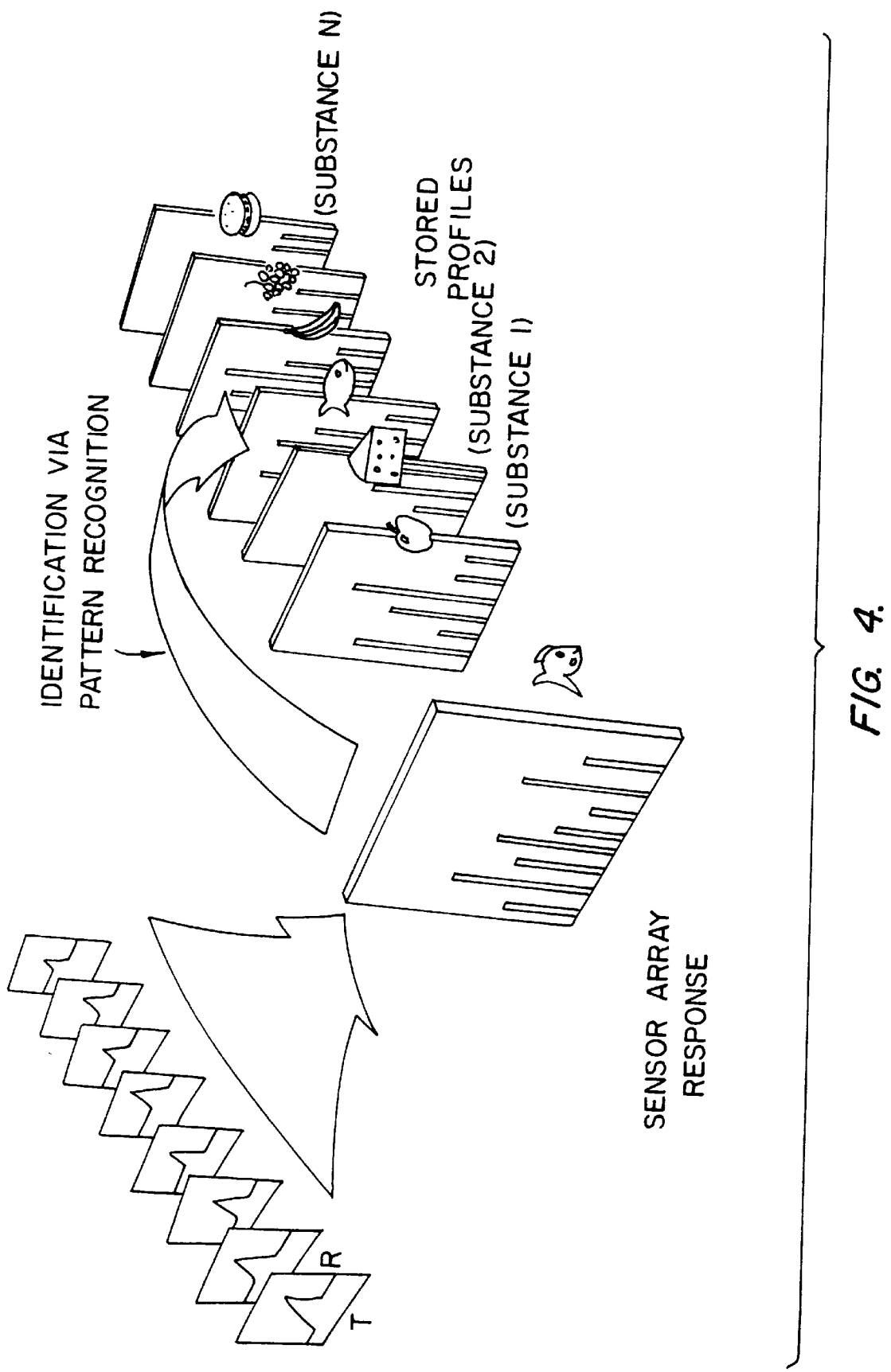
FIG. 4 is a schematic view of several different sets of response signals produced by the sensor array of FIG. 3 when exposed to several known analytes.

FIG. 3 depicts an array 25 of eight sensors like the sensor 21 of FIG. 2. Each sensor in the array has a unique formulation, such that it responds in a unique manner to any analyte brought into contact with the array. Representative response signals produced by the eight sensors in the array for one particular analyte are included in FIG. 3. These response signals are appropriately processed, as is described below, to identify the analyte to which the array is exposed. Thus, as shown in FIG. 4, the eight sensors provide response signals that form a unique pattern, or "signature," for each of a variety of known analytes. The particular response signals that are produce for an unknown analyte are correlated with a library of known signatures, to determine the closest fit and, thereby, to identify the unknown analyte.

Suitable circuitry for measuring the resistances of the sensor array 25 is disclosed in copending application for U.S. patent Ser. No. 09/178,443 filed Oct. 23, 1998, and entitled "Portable Vapor Sensing Apparatus." That copending application is incorporated by reference.

A wide variety of conductive materials and nonconductive organic polymer materials can be used. Table 1 provides exemplary conductive materials for use in resistor fabrication; mixtures, such as of those listed, may also be used. Table 2 provides exemplary nonconductive organic polymer materials; blends and copolymers, such as of the polymers listed here, may also be used. Combinations, concentrations, blend stoichiometries, percolation thresholds, etc. are readily determined empirically by fabricating and screening prototype resistors (chemiresistors) as described below.

TABLE 1

| Major Class | Examples |
| --- | --- |
| Organic Conductors | conducting polymers (poly(anilines), poly(thiophenes), poly(pyrroles), poly(acetylenes), etc.)), carbonaceous materials (carbon blacks, graphite, coke, $C_{60}$, etc.), charge transfer complexes (tetramethylparaphenylenediamine-chloranile, alkali metal tetracyanoquinodimethane complexes, tetrathiofulvalene halide complexes, etc.), etc. |
| Inorganic Conductors | metals and metal alloys (Ag, Au, Cu, Pt, AuCu alloy, etc.), highly doped semiconductors (Si, GaAs, InP, $MoS_2$, $TiO_2$, etc.), conductive metal oxides ($In_2O_3$, $SnO_2$, $Na_xPt_3O_4$, etc.), superconductors ($YBa_2Cu_3O_7$, $Tl_2Ba_2Ca_2Cu_3O_{10}$, etc.), etc. |
| Mixed inorganic/organic Conductors | Tetracyanoplatinate complexes, Iridium halocarbonyl complexes, stacked macrocyclic complexes, etc. |

TABLE 2

| Major Class | Examples |
| --- | --- |
| Main-chain carbon polymers | poly(dienes), poly(alkenes), poly(acrylics), poly(methacrylics), poly(vinyl ethers), poly(vinyl thioethers), poly(vinyl alcohols), poly(vinyl ketones), poly(vinyl halides), poly(vinyl nitriles), poly(vinyl esters), poly(styrenes), poly(arylenes), etc. |
| Main-chain acyclic heteroatom polymers | poly(oxides), poly(carbonates), poly(esters), poly(anhydrides), poly(urethanes), poly(sulfonates), poly(siloxanes), poly(sulfides), poly(thioesters), poly(sulfones), poly(sulfonamides), poly(amides), poly(ureas), poly(phosphazenes), poly(silanes), poly(silazanes), etc. |
| Main-chain heterocyclic polymers | poly(furan tetracarboxylic acid diimides), poly(benzoxazoles), poly(oxadiazoles), poly(benzothiazinophenothiazines), poly(benzothiazoles), poly(pyrazinoquinoxalines), poly(pyromellitimides), poly(quinoxalines), poly(benzimidazoles), poly(oxindoles), poly(oxoisoindolines), poly(dioxoisoindolines), poly(triazines), poly(pyridazines), poly(piperazines), poly(pyridines), poly(piperidines), poly(triazoles), poly(pyrazoles), poly(pyrrolidines), poly(carboranes), poly(oxabicyclononanes), poly(dibenzofurans), poly(phthalides), poly(acetals), poly(anhydrides), carbohydrates, etc. |

The chemiresistors can be fabricated by many techniques such as, but not limited to, solution casting, suspension casting, and mechanical mixing. In general, solution cast routes are advantageous because they provide homogeneous structures and ease of processing. With solution cast routes, resistor elements may be easily fabricated by spin, spray or dip coating. Since all elements of the resistor must be soluble, however, solution cast routes are somewhat limited in their applicability. Suspension casting still provides the possibility of spin, spray or dip coating but more heterogeneous structures than with solution casting are expected. With mechanical mixing, there are no solubility restrictions since it involves only the physical mixing of the resistor components, but device fabrication is more difficult since spin, spray and dip coating are no longer possible. A more detailed discussion of each of these follows.

For systems where both the conducting and non-conducting media or their reaction precursors are soluble in a common solvent, the chemiresistors can be fabricated by solution casting. The oxidation of pyrrole by phosphomolybdic acid presented herein represents such a system. In this reaction, the phosphomolybdic acid and pyrrole are dissolved in tetrahydrofuran (THF) and polymerization occurs upon solvent evaporation. This allows for THF soluble non-conductive polymers to be dissolved into this reaction mixture thereby allowing the blend to be formed in a single step upon solvent evaporation. The choice of non-conductive polymers in this route is, of course, limited to those that are soluble in the reaction media. For the poly(pyrrole) case described above, preliminary reactions were performed in THF, but this reaction should be generalizable to other non-aqueous solvent such as acetonitrile or ether. A variety of permutations on this scheme are possible for other conducting polymers. Some of these are listed below. Certain conducting polymers, such as substituted poly-(cyclooctatetraenes), are soluble in their undoped, non-conducting state in solvents such as THF or acetonitrile. Consequently, the blends between the undoped polymer and plasticizing polymer can be formed from solution casting. After which, the doping procedure (exposure to $I_2$ vapor, for instance) can be performed on the blend to render the substituted poly(cyclooctatetraene) conductive. Again, the choice of non-conductive polymers is limited to those that are soluble in the solvents that the undoped conducting polymer is soluble in and to those stable to the doping reaction. Certain conducting polymers can also be synthesized via a soluble precursor polymer. In these cases, blends between the precursor polymer and the non-conducting polymer can first be formed followed by chemical reaction to convert the precursor polymer into the desired conducting polymer. For instance poly(p-phenylene vinylene) can be synthesized through a soluble sulfonium precursor. Blends between this sulfonium precursor and the non-conductive polymer can be formed by solution casting. After which, the blend can be subjected to thermal treatment under vacuum to convert the sulfonium precursor to the desired poly(p-phenylene vinylene).

In suspension casting, one or more of the components of the resistor is suspended and the others dissolved in a common solvent. Suspension casting is a rather general technique applicable to a wide range of species, such as carbon blacks or colloidal metals, which can be suspended in solvents by vigorous mixing or sonication. In one application of suspension casting, the non-conductive polymer is dissolved in an appropriate solvent (such as THF, acetonitrile, water, etc.). Colloidal silver is then suspended in this solution and the resulting mixture is used to dip coat electrodes.

Mechanical mixing is suitable for all of the conductive/non-conductive combinations possible. In this technique, the materials are physically mixed in a ball-mill or other mixing device. For instance, carbon black: non-conductive polymer composites are readily made by ball-milling. When the non-conductive polymer can be melted or significantly softened without decomposition, mechanical mixing at elevated temperature can improve the mixing process. Alternatively, composite fabrication can sometimes be improved by several sequential heat and mix steps.

Once fabricated, the individual elements can be optimized for a particular application by varying their chemical make up and morphologies. The chemical nature of the resistors determines to which analytes they will respond and their ability to distinguish different analytes. The relative ratio of conductive to insulating components determines the magnitude of the response since the resistance of the elements becomes more sensitive to sorbed molecules as the percolation threshold is approached. The film morphology is also important in determining response characteristics. For instance, thin films respond more quickly to analytes than do thick ones. Hence, with an empirical catalogue of information on chemically diverse sensors made with varying ratios of insulating to conducting components and by differing fabrication routes, sensors can be chosen that are appropriate for the analytes expected in a particular application, their concentrations, and the desired response times. Further optimization can then be performed in an iterative fashion as feedback on the performance of an array under particular conditions becomes available.

The resistor may itself form a substrate for attaching the lead or the resistor. For example, the structural rigidity of the resistors may be enhanced through a variety of techniques: chemical or radiation cross-linking of polymer components (dicumyl peroxide radical cross-linking, UV-radiation cross-linking of poly(olefins), sulfur cross-linking of rubbers, e-beam cross-linking of Nylon, etc.), the incorporation of polymers or other materials into the resistors to enhance physical properties (for instance, the incorporation of a high molecular weight, high transition metal (Tm) polymers), the incorporation of the resistor elements into supporting matrices such as clays or polymer networks (forming the resistor blends within poly-(methylmethacrylate) networks or within the lamellae of montmorillonite, for instance), etc. In another embodiment, the resistor is deposited as a surface layer on a solid matrix which provides means for supporting the leads. Typically, the matrix is a chemically inert, non-conductive substrate such as a glass or ceramic.

Sensor arrays particularly well-suited to scaled up production are fabricated using integrated circuit (IC) design technologies. For example, the chemiresistors can easily be integrated onto the front end of a simple amplifier interfaced to an A/D converter to efficiently feed the data stream directly into a neural network software or hardware analysis section. Micro-fabrication techniques can integrate the chemiresistors directly onto a micro-chip which contains the circuitry for analogue signal conditioning/processing and then data analysis. This provides for the production of millions of incrementally different sensor elements in a single manufacturing step using ink-jet technology. Controlled compositional gradients in the chemiresistor elements of a sensor array can be induced in a method analogous to how a color ink-jet printer deposits and mixes multiple colors. However, in this case rather than multiple colors, a plurality of different polymers in solution which can be deposited are used. A sensor array of a million distinct elements only requires a 1 cm×1 cm sized chip employing lithography at the 10 $\mu$m feature level, which is within the capacity of conventional commercial processing and deposition methods. This technology permits the production of sensitive, small-sized, stand-alone chemical sensors.

Preferred sensor arrays have a predetermined inter-sensor variation in the structure or composition of the nonconductive organic polymer regions. The variation may be quantitative and/or qualitative. For example, the concentration of the nonconductive organic polymer in the blend can be varied across sensors. Alternatively, a variety of different organic polymers may be used in different sensors. An electronic nose for detecting an analyte in a fluid is fabricated by electrically coupling the sensor leads of an array of compositionally different sensors to an electrical measuring device. The device measures changes in resistivity at each sensor of the array, preferably simultaneously and preferably over time. Frequently, the device includes signal processing means and is used in conjunction with a computer and data structure for comparing a given response profile to a structure-response profile database for qualitative and quantitative analysis. Typically such a nose comprises at least ten, usually at least 100, and often at least 1000 different sensors though with mass deposition fabrication techniques described herein or otherwise known in the art, arrays of on the order of at least $10^6$ sensors are readily produced.

Polymers may be applied directly to the base matrix, or, monomers may be applied first and then polymerized in situ via textbook-standard polymerization chemistry. The robustness of sensors required for certain environments limits the diversity of the polymers which can be used to create arrays for these environments. Robust arrays are used for harsh environments, e.g., automobile tailpipes, and less robust arrays with greater variation in product application are used in non-chemically-corrosive environments. The polymer is determined by one skilled in the art and is application dependent. Factors relating to the specific application, which may limit the choice of sensors for certain arrays, are taken into account. Realizing that a low number of sensors with adequate, but not exhaustive, chemical diversity suffices for most applications, many applications are supported by arrays that are made of only a few sensors.

In operation, each resistor provides a first electrical resistance between its conductive leads when the resistor is contacted with a first fluid comprising a chemical analyte at a first concentration, and a second electrical resistance between its conductive leads when the resistor is contacted with a second fluid comprising the same chemical analyte at a second different concentration. The fluids may be liquid or gaseous in nature. The first and second fluids may reflect samples from two different environments, a change in the concentration of an analyte in a fluid sampled at two time points, a sample and a negative control, etc. The sensor array necessarily comprises sensors which respond differently to a change in an analyte concentration, i.e., the difference between the first and second electrical resistance of one sensor is different from the difference between the first second electrical resistance of another sensor.

In a preferred embodiment, the temporal response of each sensor (resistance as a function of time) is recorded. The temporal response of each sensor may be normalized to a maximum percent increase and percent decrease in resistance which produces a response pattern associated with the exposure of the analyte. By iterative profiling of known analytes, a structure-function database correlating analytes and response profiles is generated. Unknown analyte may then be characterized or identified using response pattern comparison and recognition algorithms. Accordingly, analyte detection systems comprising sensor arrays, an electrical measuring devise for detecting resistance across each chemiresistor, a computer, a data structure of sensor array response profiles, and a comparison algorithm are provided.

In another embodiment, the electrical measuring device is an integrated circuit comprising neural network-based hardware and a digital-analog converter (DAC) multiplexed to each sensor, or a plurality of DACs, each connected to different sensor(s).

The sensor arrays of the present invention respond to complex chemical patterns in the vapors of different environments, and through their associated neural network, learn what the different patterns mean. The sensor arrays are not designed as classical sensor to be used for the precise measurement of specific analytes. Rather, the arrays are configured to mimic the function of the mammalian nose, and are subject to the same operating advantages and disadvantages encountered by the mammalian nose. The arrays, like the nose, can mistake one stimulus (a chemical; a smell) for another, and they can have different types and levels of sensitivity over time. The sensitivity can vary from environment to environment and can register a response that is out of proportion to the stimulus actually present, i.e., a non-linear response. The sensor array can detect specific smells against complex backgrounds of other smells and further, the array need not know the component that it's detecting, nor must it correlate a specific sensation with the presence of a specific chemical or mixture of chemicals in order to function. It can screen out information that is not important and hone in on information that is.

In addition, the sensor arrays are adaptable to many different sensing tasks including: pin-pointing the location of a certain stimulus; identifying uniquely a complicated system or state of matter based upon an odor and then remembering this information for later, on-line, instantaneous differentiation of one system or state of matter over another; and registering and monitoring, on a real-time basis, changes in complicated chemical patterns without having to determine exactly the chemical sources of the change.

The general method for using the disclosed sensors, arrays and electronic noses, for detecting the presence of an analyte in a fluid involves resistively sensing the presence of an analyte in a fluid with a chemical sensor comprising first and second conductive leads electrically coupled to and separated by a chemically sensitive resistor as described above by measuring a first resistance between the conductive leads when the resistor is contacted with a first fluid comprising an analyte at a first concentration and a second different resistance when the resistor is contacted with a second fluid comprising the analyte at a second different concentration.

Figure 14A:
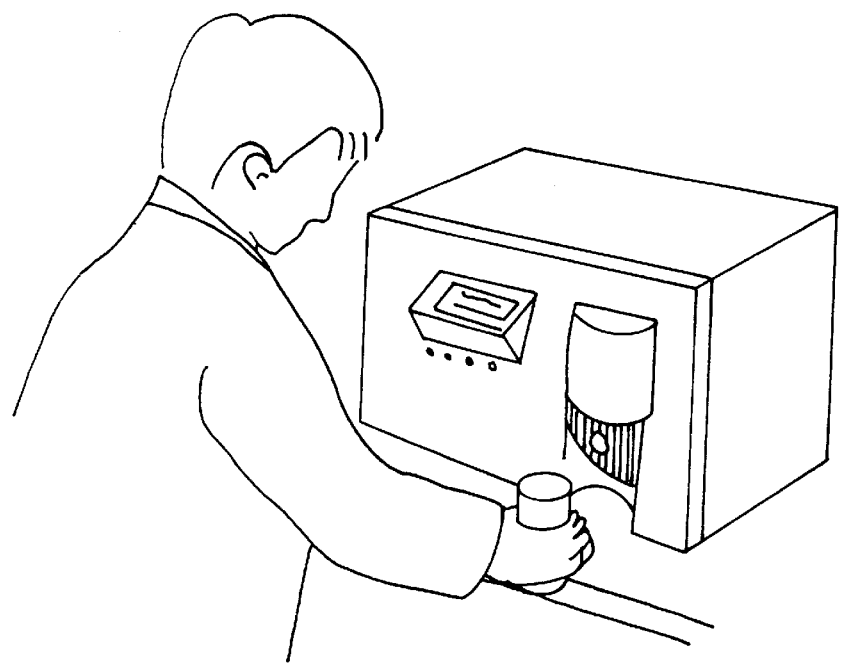
FIG. 14A is a perspective view of a tabletop device, or box-type sensor, for detecting odors, in accordance with the invention.
Figure 14B:
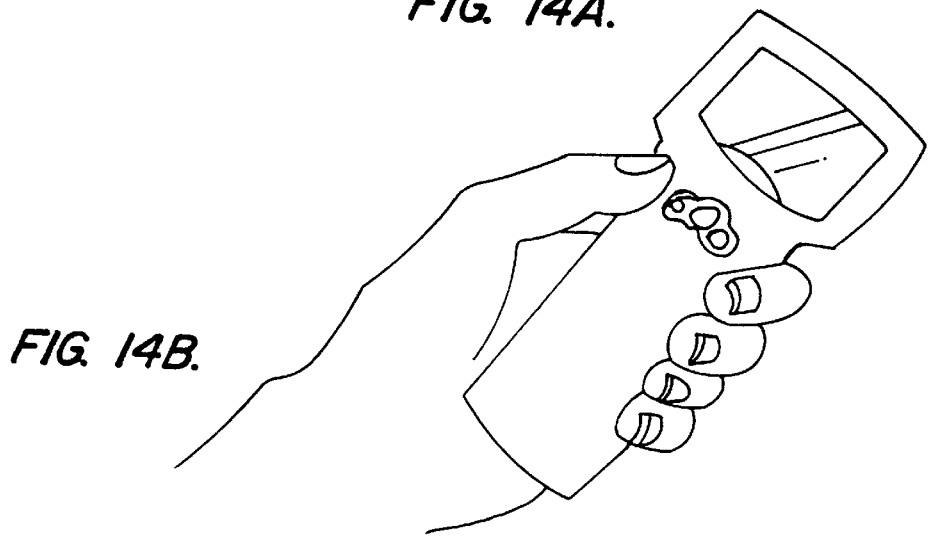
FIG. 14B is a perspective view of a hand held device for detecting odors, in accordance with the invention.
Figure 14C:
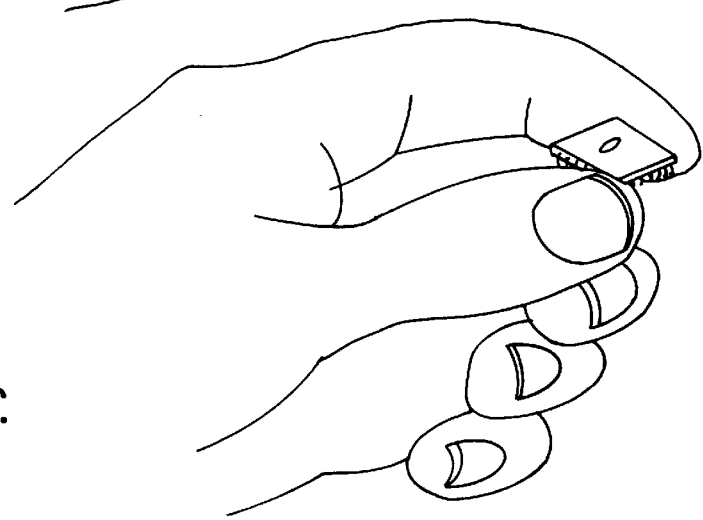
FIG. 14C is a perspective view of an integrated chip device for detecting odors, in accordance with the invention.

Three levels of applications are envisioned for the sensor based odor detection system. The three levels are: (1) a table top device (FIG. 14A); (2) a hand held device (FIG. 14B); and (3) an integrated chip based sensor (FIG. 14C). All levels of sensor based-odor detection devices contain a sensor, an electrical measuring apparatus operatively associated with each sensor; and a fluid delivery appliance.

The first system, a box-type sensor (FIG. 14A), is a small, tabletop device incorporating three components: the sensor head, discrete electronics, and application-specific fluid delivery hardware. Box-type sensors are primarily useful as product prototypes and for use in beta-sites for future applications development. This is especially true for applications, where smell profile libraries would be created from various samples.

Using standard printed circuit board (PCB) technology, a sensor head that is suitable for box-type sensors can be created. The selection of polymers to form arrays will be application-dependent. But, clean separation of various fluids can be achieved with about 20 sensors.

The discrete electronics required for box-type sensors is commercially available rudimentary circuitry. As part of the electronics package for a box-type chemical sensor application, software can provide the user interface. This involves modifying off-the-shelf neural network software. In addition, in many sensor applications, the neural net will actually be contained in software rather than embedded in a silicon chip. This leads to the requirement of a microprocessor to run the software and this may be off-the-shelf neural network software that would be pre-programmed for each application.

The application -specific hardware component includes such elements as sample delivery, sample heating (if necessary to achieve a certain vapor pressure), etc. Examples of the application-specific fluid delivery hardware includes: (1) a mask for breathalyzer type applications, (2) a wand for probe-type applications, and (3) a sample container in which sample processing (heating, cooling, etc.) could occur.

The second sensor-based odor detection system, i.e., the hand-held system, (FIG. 14B), incorporates a miniaturized sensor head placed on a silicon semiconductor chip. The sensor density on the chip must be increased for hand-held type applications from that of box-type applications. This can be achieved using PCB technology. More advanced hand-held systems possess polymers with the proper sensing and electronic properties that have been placed on silicon chips. Ink jet technology is an example of technology that can be appropriated for this purpose. As in the box-type system, the selection of polymers for the array is application specific.

The electronics of the hand-held system are essentially the electronics used in the tabletop system but with integrated signal processing. The miniaturization of the circuitry is accomplished using ASIC (Application Specific Integration Circuit) or other equivalent technology. The ASIC component requires more sophisticated design and engineering than the box-type sensor and is achieved by using known micro-process control technologies.

The sensor array and the electronics are integrated so that as much signal processing as possible based upon the original sensed smell can be accomplished at the level of the sensor array itself. Signal processing carried out some distance from the sensor head results in lost signal strength and requires higher-powered electronics. The electronics required to compensate for this loss will lead to a higher-power solution than would be desirable for some applications and would likely force up unit manufacturing costs.

Software is important in the hand-held system. The more efficient the software, the less powerful the microprocessor chip that is required. The optimal system contains a true bridge to neural net in silicon with part of the neural net software transferred onto the chip.

The third sensor-based odor detection system, the chip-based system (FIG. 14C), could be integrated universally into almost any system where active, accurate or "smart" chemical sensing would offer product or service advantages or other economic benefit. This system contains a sensor array, an electrical measuring apparatus operatively associated with the sensor, and an information storage and processing device, all of which are incorporated on a single substrate such as a silicon chip.

The chip-based system includes of two chips, with its electronic functions divided between the two chips. One chip would contain the sensor head, an application-specific, micro-machined mechanism to bring the smell to the chip in the required environment, and all signal processing electronics up until the point where the neural network takes over. The second chip would contain a microprocessor or a neural network realized in silicon. The neural network may be etched into the silicon, which eliminates the requirement for a microprocessor to run the neural net software. In general, with a neural net on the chip and no microprocessor, only micro-watt power will be required and the chip-based sensor system will be able to operate for very long periods on the equivalent of a watch battery. With the neural net in software and hence the requirement of a microprocessor, milli-watt power will be required and the chip-based sensor system will be able to run for shorter periods on the equivalent of four D-cells.

Ink jet technology is preferred for placing a large number of polymer spots on a small area to form the sensor array. The spot density may be from around 10,000 spots in a one square centimeter area to less than one hundred, depending on the application and level of sensing required for the specific application. Another technique for forming the sensor array involves using a press to force-cut and simultaneously embed a sheet containing the different polymers into the sensor bed template.

The sensor-based odor detection systems have specific application in a variety of different technological fields, including the automotive, consumer products, consumer health care, environmental monitoring and remediation, food and beverage, and petrochemical, industries. In addition, sensor-based odor detection systems have applications in industrial manufacturing, law enforcement, and hazardous materials identification, as well as diagnostic applications in the medical field. In general, the sensor technology is applicable to those molecules or odorants that have a detectable vapor pressure. Currently, the detection limit is on the order of parts per billion. Realistically, many molecules or odorants fall into this category, in particular, all volatile organics, also molecules which have evolved specifically to be transmitted as smell (e.g., pheromones), and perhaps most importantly, complex vapor-borne chemical mixtures that make up most smells—smells which cannot be attributed to any single, identifiable substance. Molecules that do not develop an appreciable vapor pressure at temperatures where the sensor technology could be used include many of the larger important bio-molecules, such as glucose, neurotransmitters, nucleic acids, proteins, etc.

A wide variety of analytes and fluids may be analyzed by the disclosed sensors, arrays and noses so long as the subject analyte is capable generating a differential response across a plurality of sensors of the array. Analyte applications include broad ranges of chemical classes such as organics such as alkanes, alkenes, alkynes, dienes, alicyclic hydrocarbons, arenes, alcohols, ethers, ketones, aldehydes, carbonyls, carbanions, polynuclear aromatics and derivatives of such organics, e.g., halide derivatives, etc., biomolecules such as sugars, isoprenes and isoprenoids, fatty acids and derivatives, etc. Accordingly, commercial applications of the sensors, arrays and noses include environmental toxicology and remediation, biomedicine, materials quality control, food and agricultural products monitoring, etc.

Complex vapor mixtures constitute a billion-year old identification, classification and communications system for which no viable detection and categorization technology exists. There are myriad potential products and applications based upon the detection of single, vapor-borne chemicals for which no technology exists. Many of these potential applications require that the chemical of interest be detected against a complex, ever-changing background of other chemicals. Since the sensors are not looking for a specific chemical, the existence of other chemicals in the background does not affect its detection ability. The sought-after chemical itself triggers one unique pattern in the array, while the sought-after chemical against a noisy chemical background simply triggers other unique patterns, all of which can be learned.

The sensors are generally applicable in two areas: (1) diagnostics and control applications; and (2) identification, categorization, and differentiation applications. The diagnostics and control applications, e.g., cars, power plants, factories, pipelines, people, involve monitoring with feedback, the ebb and flow of chemicals in complex systems. These systems are made up of multiple sub-systems each containing different concentrations of different chemicals, where the separation of the sub-systems is critical for the function of the overall system. Here, the chemical composition of the various monitoring environment may be changing constantly in an unknown and unknowable manner. The identification, categorization, and differentiation applications either are based upon specific molecular determinants that may or may not be known or are based upon complex unknown chemical mixtures, which may be changing over time.

For each application level of the sensor-based odor detection device, three modes of analyte detection are possible. The first is a single-analyte detection system, which incorporates a sensor that detects the presence or absence of a single analyte, e.g., ethylene glycol (antifreeze) in engine radiators. The second is a multiple analyte detection system, which can differentiate among and identify various chemicals in a sample, e.g., differentiating an identification of individual hydrocarbons in a petroleum product. The third is a smart detection system, which can be programmed with enough information to be able to learn how to identify the key chemical features of its environment. An example is a food-cooking monitor that can identify the various smells and vapors from the cooking of an individual food and automatically stop cooking when the cooking is complete.

In addition, a large number of sensor-type applications that are not necessarily chip-based can be foreseen. These sensor-type applications do not require complicated electronics or signal processing to achieve the desired result, but merely indicate; in the same way as does a glucose test strip, that a certain level of a specific analyte is or is not present.

The sensor-type applications can be further categorized by the type of fluid that is to be analyzed. Since the sensors are limited to the detection of vapors, the sensor-based odor detection devices must have specific hardware for delivering the sample to be analyzed. The sample delivery hardware is different for the vapor analysis of a gas, liquid, or solid sample. Specific examples of preferred embodiments for the sample delivery hardware, sensor head, and electronics for specific applications are described below. It is understood that the descriptions as provided below are given as examples of sensor-based odor detection devices and do not limit the invention to the devices represented below.

In order to achieve desired sensing applications for liquids, a shield that keeps out the liquid being analyzed but admits its vapor must separate the liquid sample from the sensor. Examples of the type of shields that may be employed in the sensor hardware include gas-permeable metal-based screens, gas-permeable polymer-based membranes, or other devices and products that allow for the permeation of gases while excluding liquids. In addition, liquid-based samples may need to be heated to achieve a vapor pressure at which specific analytes may be detected. A sample chamber for containing a liquid sample and if necessary, heating the liquid sample to a suitable vapor pressure to analyze the fluid may also be employed in the fluid delivery apparatus. The integrated system contains a fluid delivery device that is associated with the substrate containing the sensor and possesses a miniature screening apparatus and optional sample vaporization hardware associated with the substrate.

The sensing of gases is somewhat more straightforward in that the fluid being detected is already in the vapor form. The analysis of analyte already in the vapor phase requires capture and delivery of the gaseous fluid to the sensor array. Examples of capture and delivery devices include masks, probes, wands, tubes, and other devices that are capable of capturing and delivering gaseous fluids. In addition, part of the gaseous fluid delivery device may include hardware that condenses gaseous fluids and then revaporizes the fluid to achieve appropriate vapor concentration.

Analysis of fluids embedded in a solid, or a solid analyte itself, requires liberation of the fluid from the solid to a vapor. This requires a vessel capable of containing a solid and delivering the vapor liberated from the solid to the sensor.

One area of application for sensor-based odor detection devices is in the monitoring of engine fluids. Applications for chemical sensors exist wherever there is a liquid or a vapor that can leak or that can change in condition or quality over time. This includes any liquid and its vapor. These include, but are not limited to detection of analytes in radiator fluid, engine oil, transmission fluid, gasoline, diesel fuel, etc. In these applications, the sensors are used mainly in a diagnostic capacity, to improve engine performance and lower maintenance costs. In order to achieve the desired monitoring applications, the engine fluids would be separated from the sensor by a gas permeable shield. A small monitor could be installed in many regions adjacent to an engine separated from the fluid being measured by a shield that keeps out the fluid being analyzed but admits its vapor.

Figure 15:
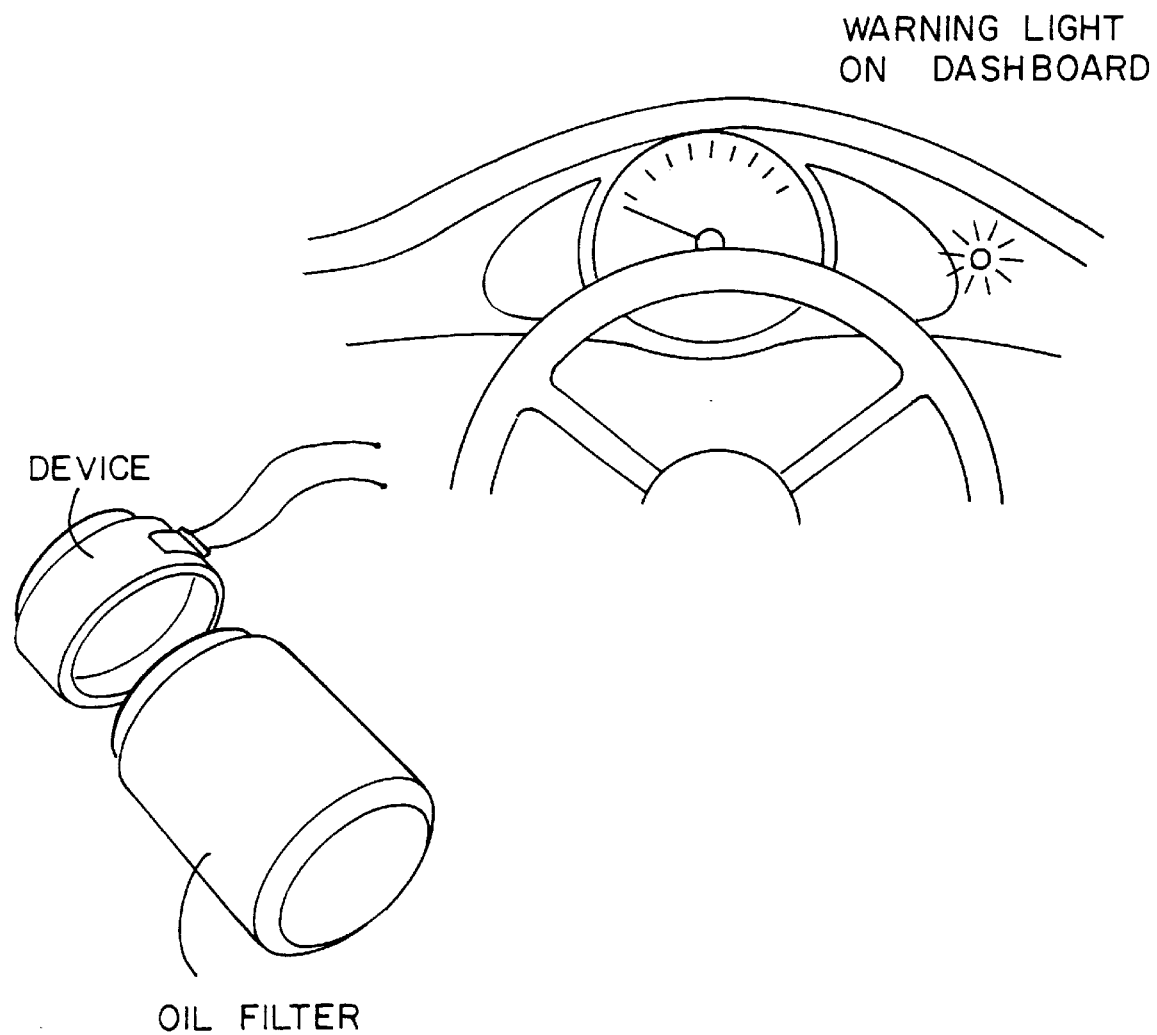
FIG. 15 is a schematic view of a sensor-based fluid detection device used as an automotive oil change monitor.

A specific example of a sensor-based fluid detection device for use in an engine application includes an oil change monitor (see FIG. 15). The number one consumer request in the automotive maintenance industry is knowledge of when to change the oil. Differentiating between good oil, which is basic, and bad oil, which is acidic, is an easy-to-detect chemical change for the sensor-based fluid detection device. Such a sensor could be put in crankcase or actually in the oil filter, in which case it could be a disposable product. Monitoring the oil quality would enable oil changes to be performed no sooner than when they are actually required. The detection of oil quality would result from a direct readout of the chemistry of the oil, rather than as is the case with some current detectors, which are based upon an algorithm that uses time, ignition firing, rpm, temperature, etc., to derive a result.

Figure 16:
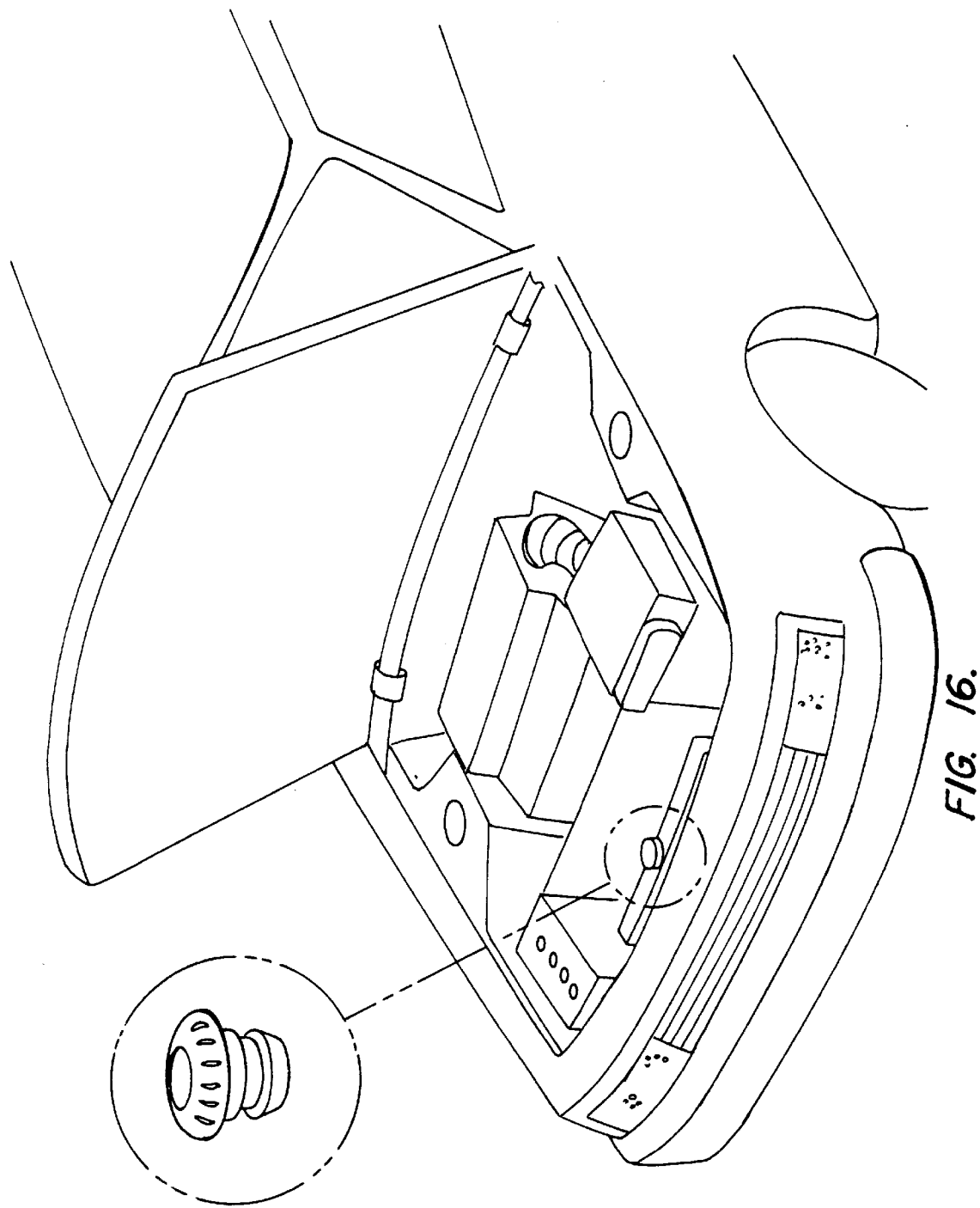
FIG. 16 is a perspective view of a sensor-based fluid detection device used as an automotive antifreeze monitor.

Another application for the sensor-based fluid detection device in engine fluids is an antifreeze monitor (see FIG. 16). A sensor could be placed in a radiator cap to determine if sufficient antifreeze (ethylene glycol) is present. This is a straightforward application for the sensor-based fluid detection technology, since a single, known chemical must be detected. The radiator cap could simply incorporate a chip tuned for ethylene glycol concentration. This would counteract user error in providing a warning when insufficient antifreeze is present. This is an especially useful application in extreme climates, where insufficient antifreeze can cause significant engine damage.

Control application sensors collect information from a certain environment within an engine, and then feed this information to on-board computers, which in turn use the information to manage and optimize the engine's operation. The information could be used to diagnose engine problems, fluid quality problems, etc.

Diesel engines can burn many fuels, but their mechanical durability is based upon the presence or absence of a few key elements in the fuel. These elements include certain sulfur compounds, asphaltenes, and other elements, which effectively polymerize and function as engine lubricants. Sensing them is critical to maintaining engine longevity. The sensors can distinguish among various different hydrocarbon species, e.g., asphaltenes vs. diaspheletenes vs. parafins vs. olefins, etc., and engine operation can be adjusted in accordance with the sensed fuel components.

In addition, with increasingly tighter emissions standards, automobiles are being pushed toward operating on different fuels, e.g., gasahol, and operating on gasoline as efficiently as possible. Therefore, fuel quality monitoring is becoming increasingly important. One way to address such automotive applications is to use a neural network, which can be used to measure the air/fuel ratio to optimize fuel efficiency.

Figure 17:
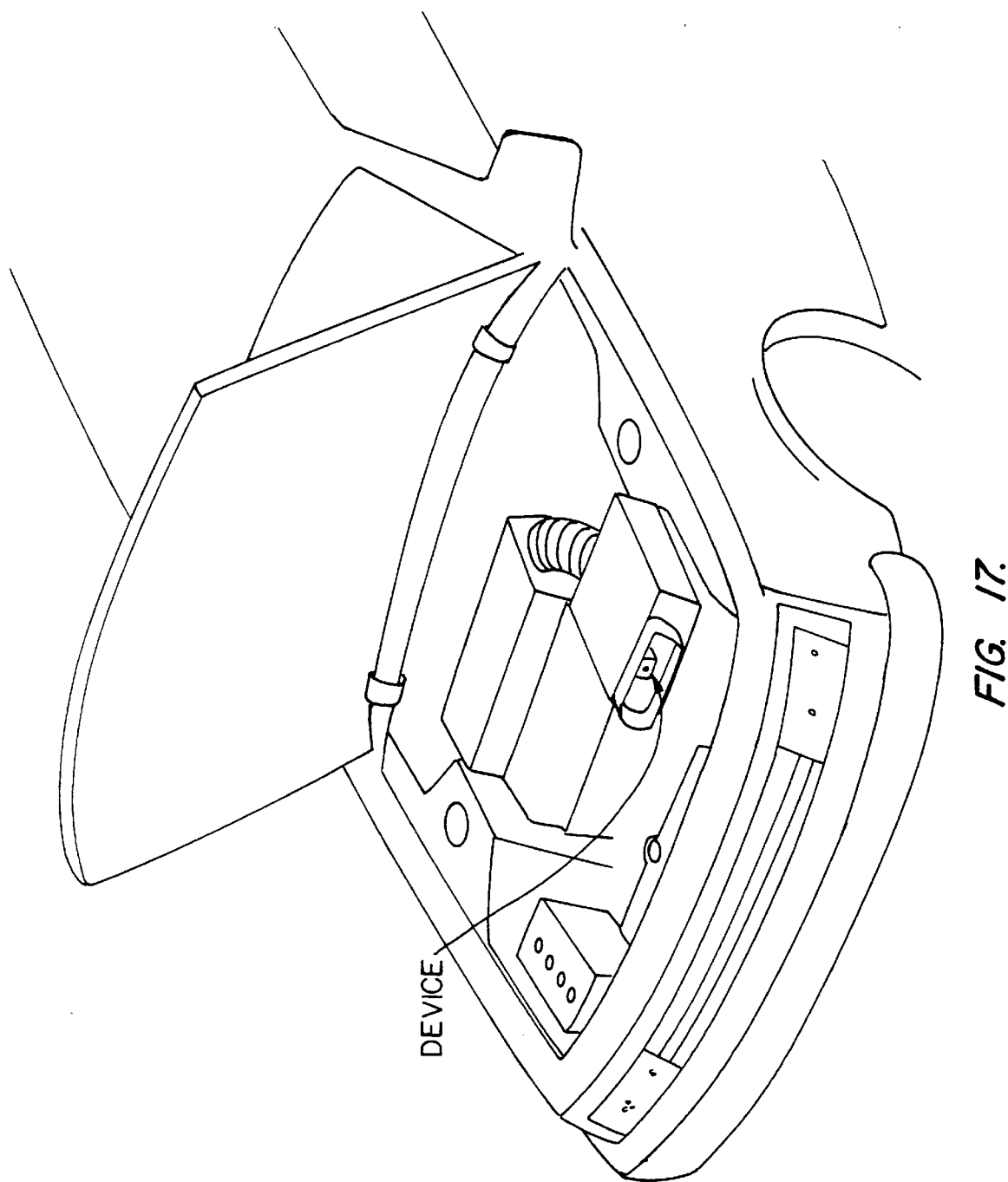
FIG. 17 is a perspective view of a sensor-based fluid detection device used to monitor and detect emissions in the intake system of an automobile's internal combustion engine.
Figure 18:
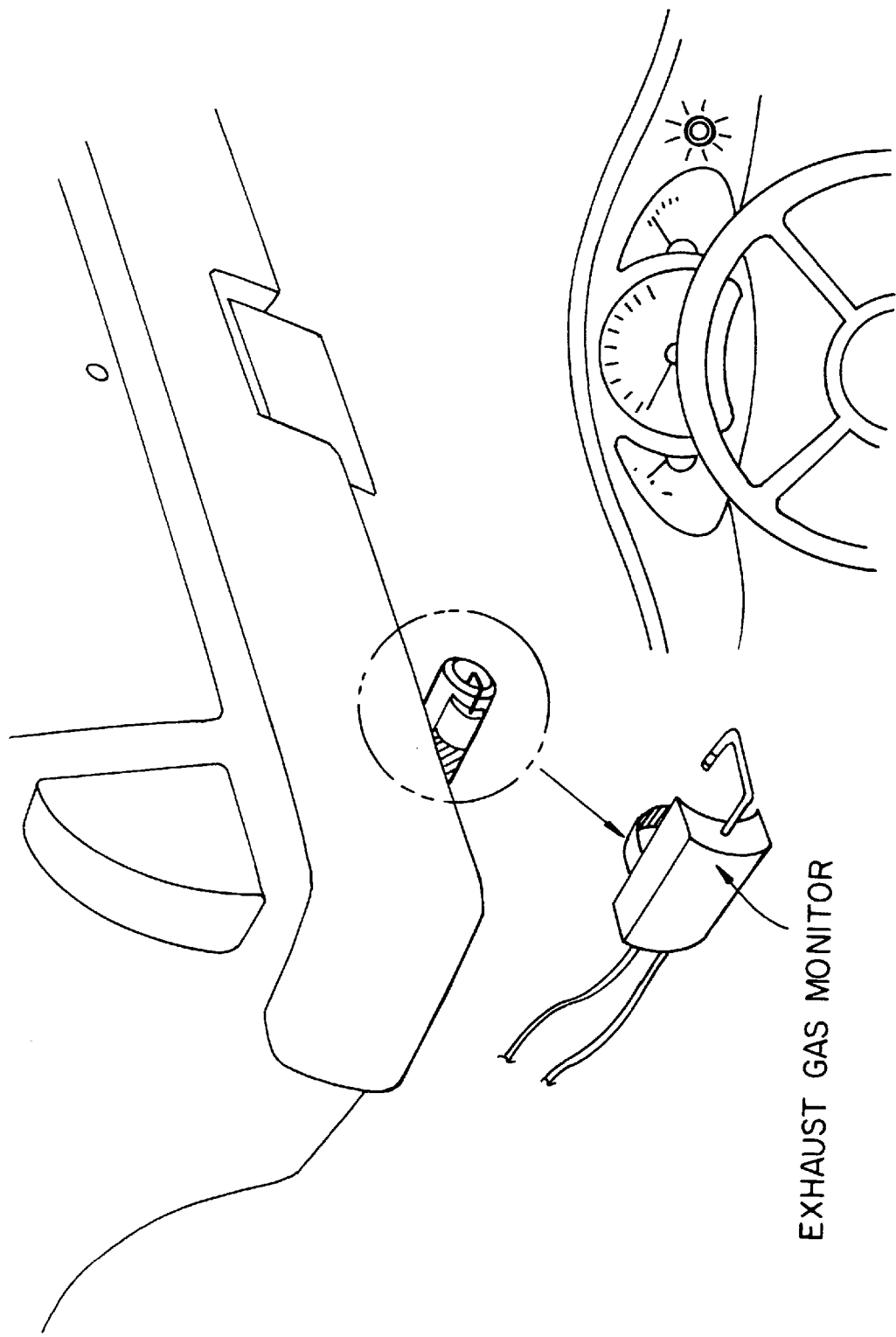
FIG. 18 is a schematic view of a sensor-based fluid detection device used to monitor and detect emissions in the exhaust system of an automobile's internal combustion engine.

In another preferred embodiment of the invention, the sensor-based fluid detection device is used for monitoring and detecting emissions from combustion processes. Polymer-based sensors can be placed in either the engine intake (FIG. 17) or the exhaust (FIG. 18) for use in cleanburn emissions control. The sensor located in the engine intake would not measure emissions directly. Rather, the measurements taken at the intake would be put through a neural network using the automobile's on-board computer and would impute emissions quality from the sensor information and information from other sensors present in the automobile. Sensors could also be placed in the exhaust, but high temperature exhaust systems would require insulation of the sensor from the harsh temperature environment.

Examples of such combustion processes include automotive gasoline and diesel engines as well as industrial combustion processes such as power plant emissions. The sensors also could detect catalyst function and readily determine if conversion of combustion products such as volatile organic compounds (VOC's) is complete. A small integrated sensor that could detect emissions products such as VOC's, $NO_x$, $SO_x$, $CO_2$ and water, for example, could alert engine operators and industrial combustion operators (e.g., power plant operators), whether combustion is complete and if the emission reducing catalytic converters are functioning properly.

Metal oxide sensors are used currently for some applications, e.g., monitoring exhaust gases. Their disadvantage, when as application-specific sensors, is cost and the requirement that they be heated. This can lead them to act as an ignition source, which is dangerous in areas such as this with combustible gases.

Figure 19:
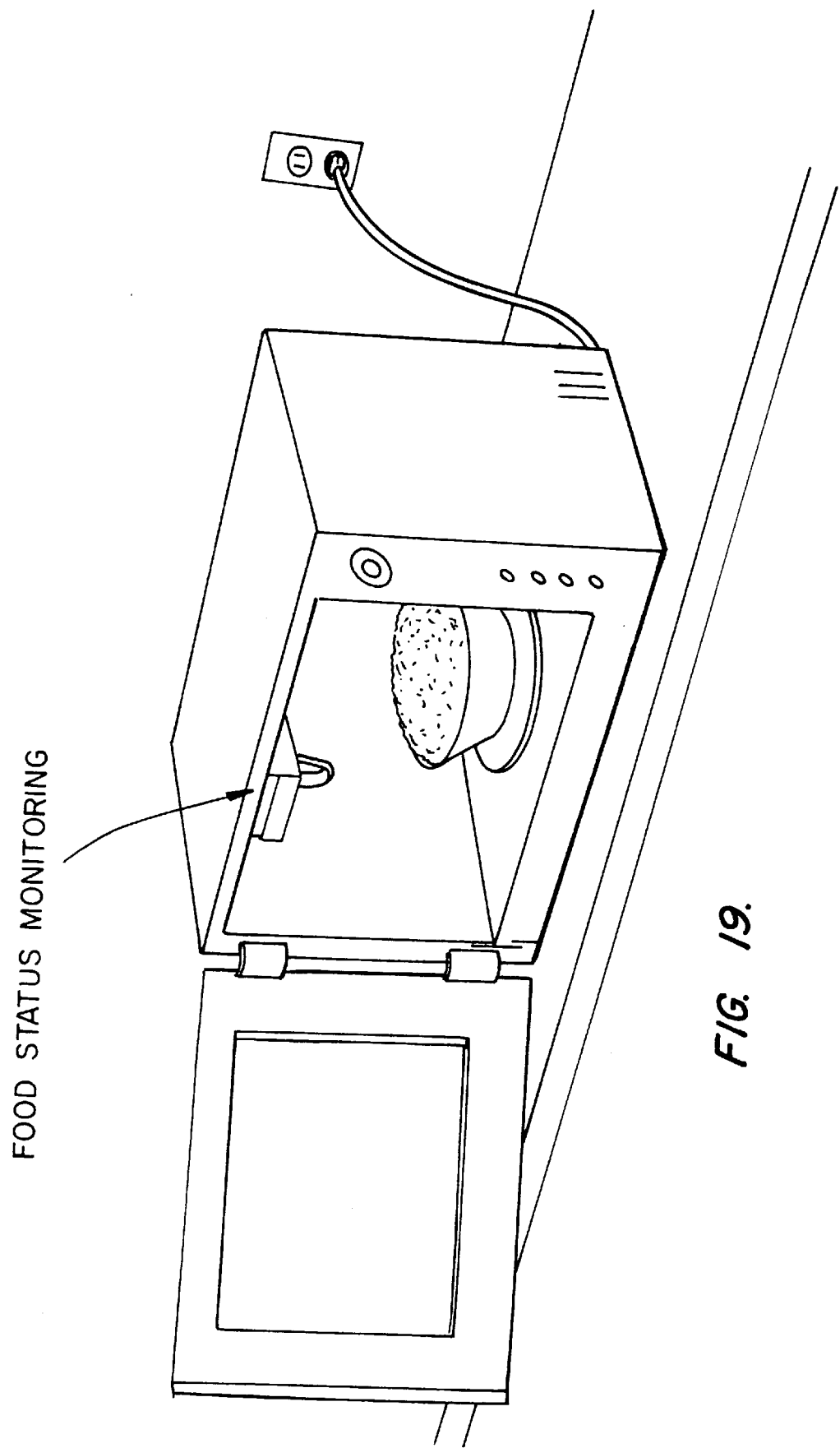
FIG. 19 is a perspective view of a sensor-based fluid detection system used to monitor and detect emissions from cooking and heating food.

In other preferred embodiments of the invention (see FIG. 19), the sensor-based fluid detection system is used for monitoring and detecting emissions from food cooking and heating processes. In one embodiment, the sensor is employed in microwave cooking without the need to set temperature or time. One button operation of microwave cooking would be possible, i.e., "Cook" with a sensor for humidity, which is essentially, water vapor. The neural network predicts the temperature rise profile, and in a control loop adjusts the amount of heating (microwave energy) required.

In another embodiment, the sensor-based fluid detection array would be combined with a neural network programmed to optimally cook a whole spectrum of food types, along with profiles of their evolving smells as they cook. For example, green beans would be placed into the microwave oven and the oven recognizes the first vapors of green beans beginning to cook and follows the green bean optimal microwave energy profile. Ongoing monitoring would enable real-time adjustment, i.e., as the green beans approach being fully cooked, they could be tested by the smell sensor and energy reduced or increased and the cooking time modified. In this way, food thickness, wetness and other qualities could be automatically adjusted for.

Figure 20:
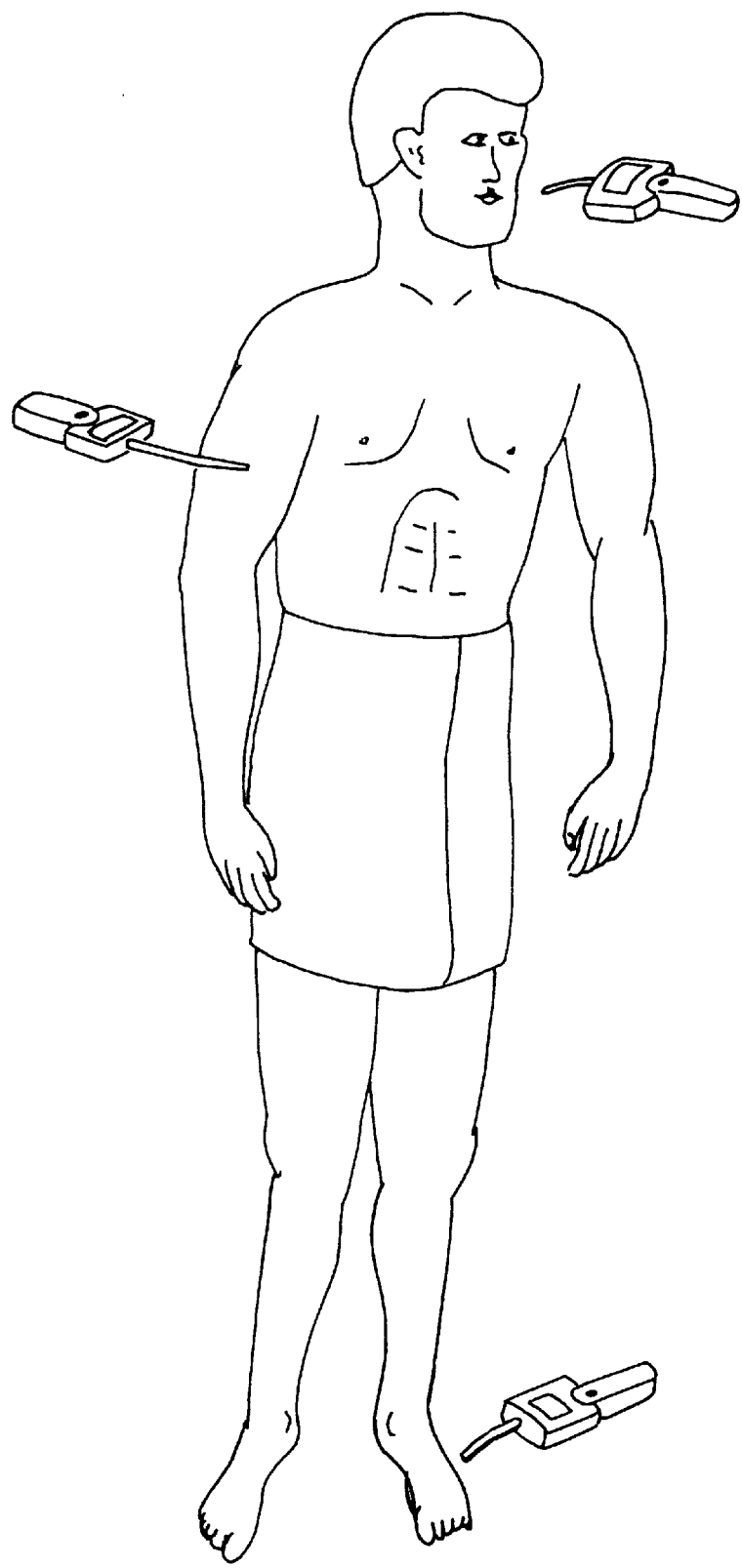
FIG. 20 is a perspective view of a hand held sensor-based fluid detection system for use in monitoring and detecting personal body odors.

Another preferred embodiment for the sensor-based fluid detection system is a personal odor detection device (see FIG. 20). Individuals generally cannot detect their own body odor, e.g., bad breath, underarm odor, etc. Halitosis in particular is a common hygiene problem that is not readily self detectable. A sensor-based odor detection device comprised of a sensor, a fluid delivery device, an electronic measuring device, and an information storage and processing device can detect the presence of human breath vapors. Neural network software attached to the sensor array can compare the human breath vapors with a library of bad breath smells and provide a response to indicate the presence of unpleasant odors.

Figure 21:
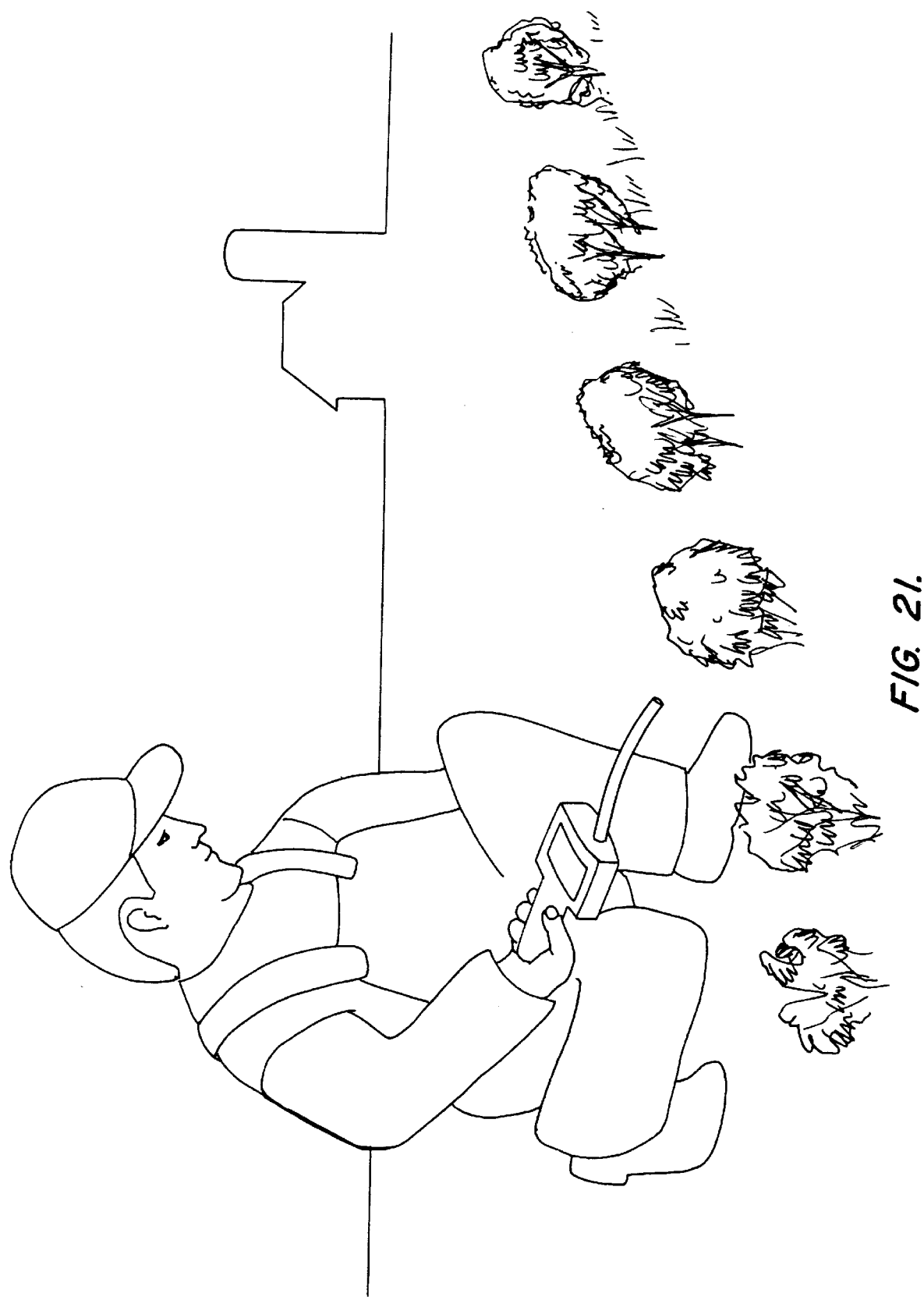
FIG. 21 is a perspective view of a hand held sensor-based fluid detection system for use in soil analysis.

Another preferred embodiment is a sensor-based fluid detection device for soil analysis (see FIG. 21). Organic soil contaminants are currently analyzed using lab-based gas chromatography. A portable sensor-based fluid detection device would allow for on-site analysis of soil contamination. A sensor-based fluid detection device can detect contaminants found at contaminated sites either by a box-type sensor, which could detect the presence of any volatile soil contaminants, or by a higher level sensor that would be able to separately detect individual analytes in a soil sample. This is particularly useful in soil remediation applications, where rapid, automated, parallel processing of multiple analytes in the field is desirable.

Figure 22:
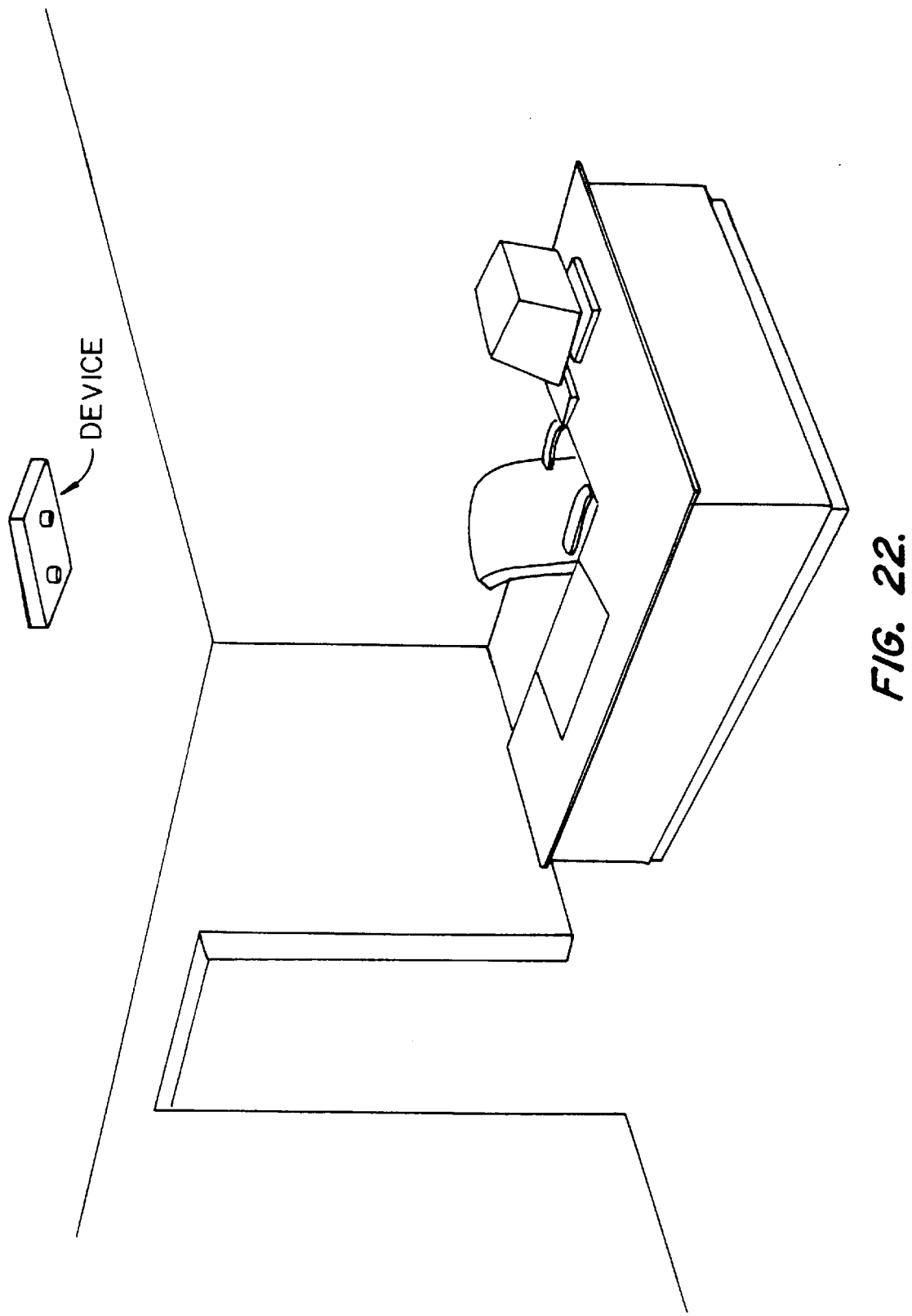
FIG. 22 is a perspective view of a sensor-based fluid detection system for monitoring the environmental conditions within an office.

Another preferred embodiment is a sensor-based fluid detection device for environmental monitoring (see FIG. 22). Environmental monitoring and air quality control of atmospheric gases such as water vapor (humidity), CO, oxygen, ozone, etc., as well as volatile organic chemicals (solvents) and noxious or unpleasant gases, could be performed by a sensor-based fluid detection device. The sensors have a variety of useful settings including homes, office buildings, industrial manufacturing facilities, laboratories, etc., and could be installed in thermostats or as a separate environmental monitoring unit.

Figure 23:
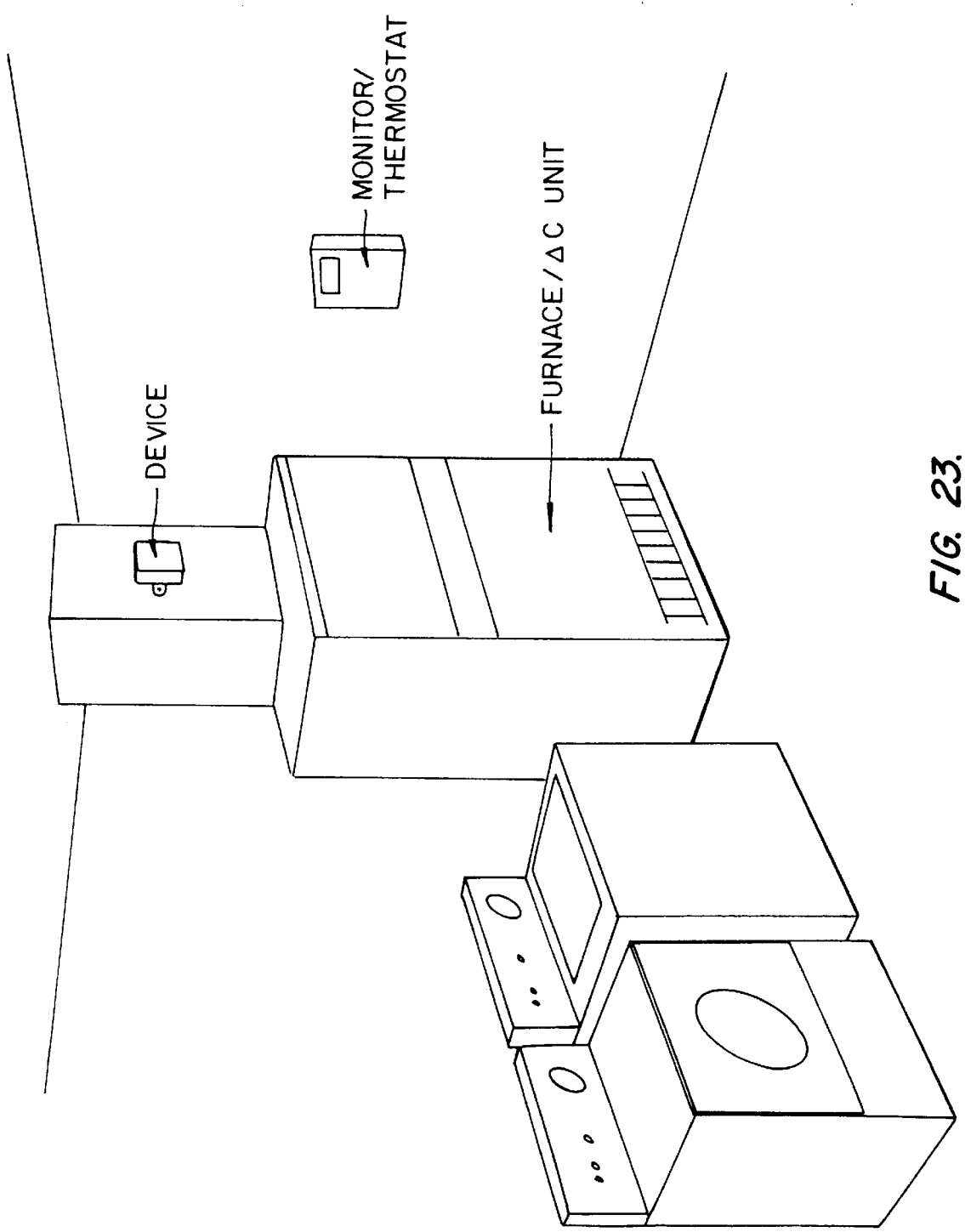
FIG. 23 is a perspective view of a sensor-based fluid detection system that is part of a modern HVAC system, for use in controlling environmental conditions in homes and buildings.

As shown in FIG. 23, the sensor could be part of an active feedback loop, especially for homes or buildings with modem HVAC systems. The air quality sensor would function in a manner similar to a thermostat. Recirculation, oxygen and carbon dioxide levels could be continuously monitored and adjusted, just as temperature is currently monitored and adjusted using a thermostat. Another example of an environmental monitoring application is in the passenger cabins of automobiles and airplanes, or other small self-contained environments. In particular, a sensor that detects atmospheric vapors such as humidity, carbon monoxide, and oxygen, in combination with a sensor that detects noxious or unpleasant vapors and a recirculation/fresh air control device, depending on the indoor/outdoor air quality, is an example of an embodiment useful for automobiles or other enclosed spaces. For example, a sensor device in an automobile, upon passing an odiferous garbage truck, would detect the odor and immediately switch the environmental control from "Fresh Air" to "Recirculate." Conversely, the sensing device, upon detecting excess carbon monoxide in the automobile compartment, would automatically switch to "Fresh Air."

Figure 24:
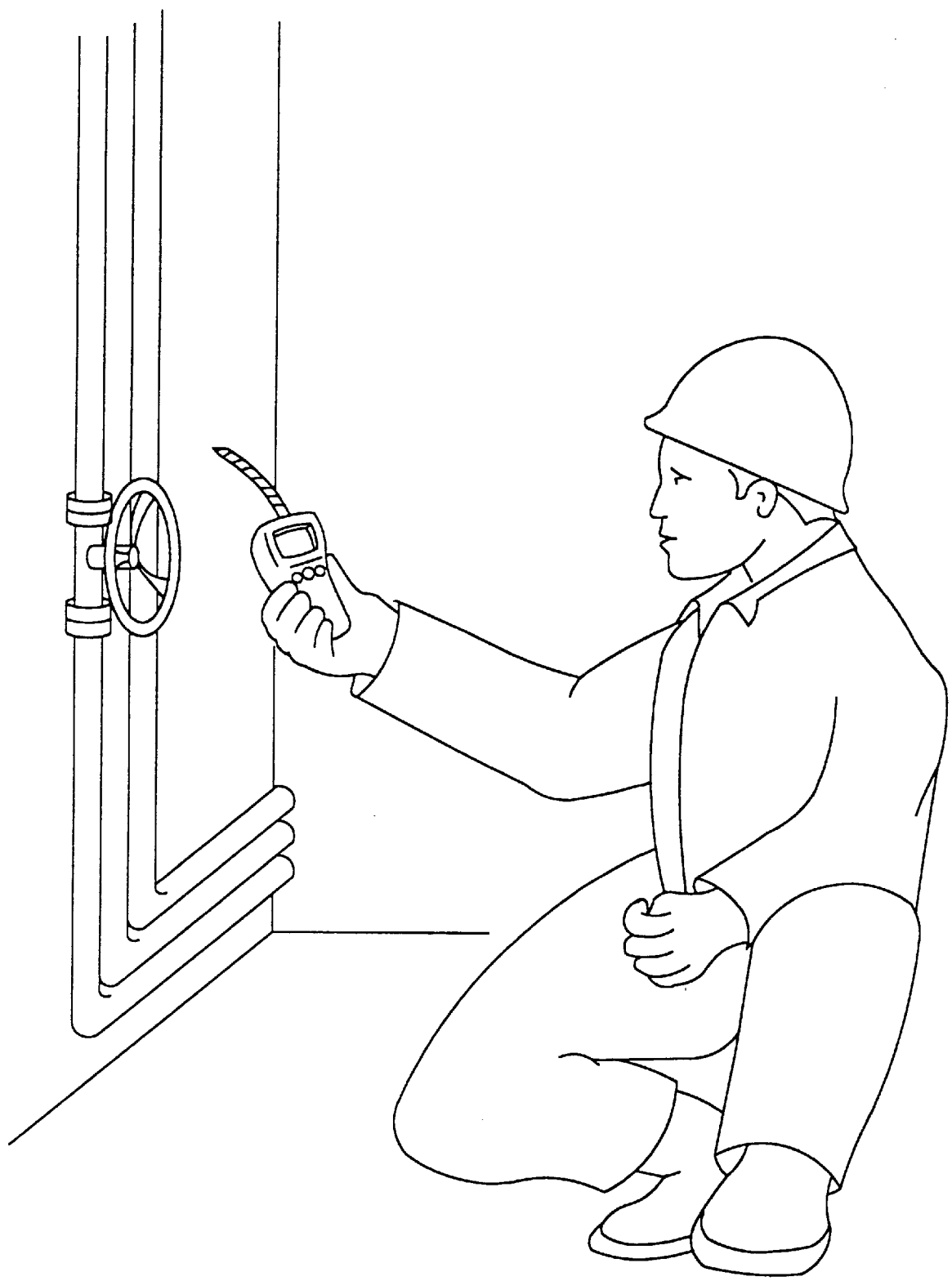
FIG. 24 is a perspective view of a hand held sensor-based fluid detection system used to detecting leaks in an industrial manufacturing plant.

The sensor devices also are applicable to petroleum refining plants, laboratories, and industrial manufacturing plants where volatile chemicals are used and monitored (see FIG. 24). In petroleum refining plants, machinery, storage tanks, pipelines, etc. must be inspected frequently for leaks, and a sensor-based odor detection device, particularly a portable device, could be used for inspecting and monitoring for fluid leakage and spills. A related application for the sensors is detecting leaks in underground storage tanks, pipelines and other relatively inaccessible processing and storage facilities for hazardous chemicals such as petrochemicals. Chemical plants are yet another example of complex systems where on-line chemical monitoring is useful, either to actuate alarms or to be made part of active process control feedback loops.

Monitors for industrial coatings, paint and curing processes can employ the same basic sensor technology. Currently, these processes are monitored based on a recipe (time and temperature). A sensor-based fluid detection device could alert plant operators when the processes were complete, e.g., actuate a notification device when the paint is dry, the plastic cured, etc. Installed models would be useful for drying rooms in industrial plants and on assembly lines.

Figure 25:
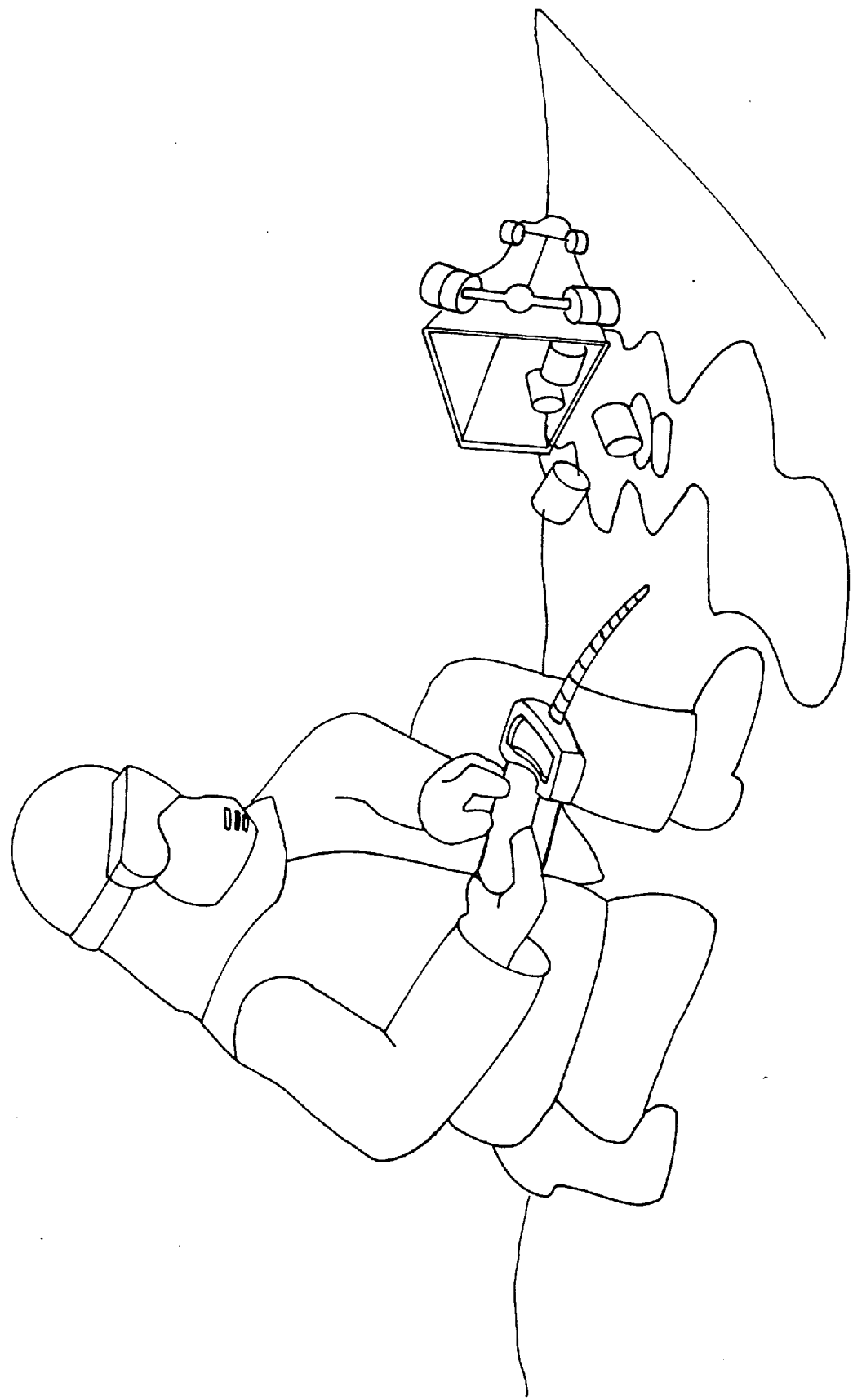
FIG. 25 is a perspective view of a hand held sensor-based fluid detection system used to detect and identify hazardous materials that have been accidentally spilled.
Figure 26:
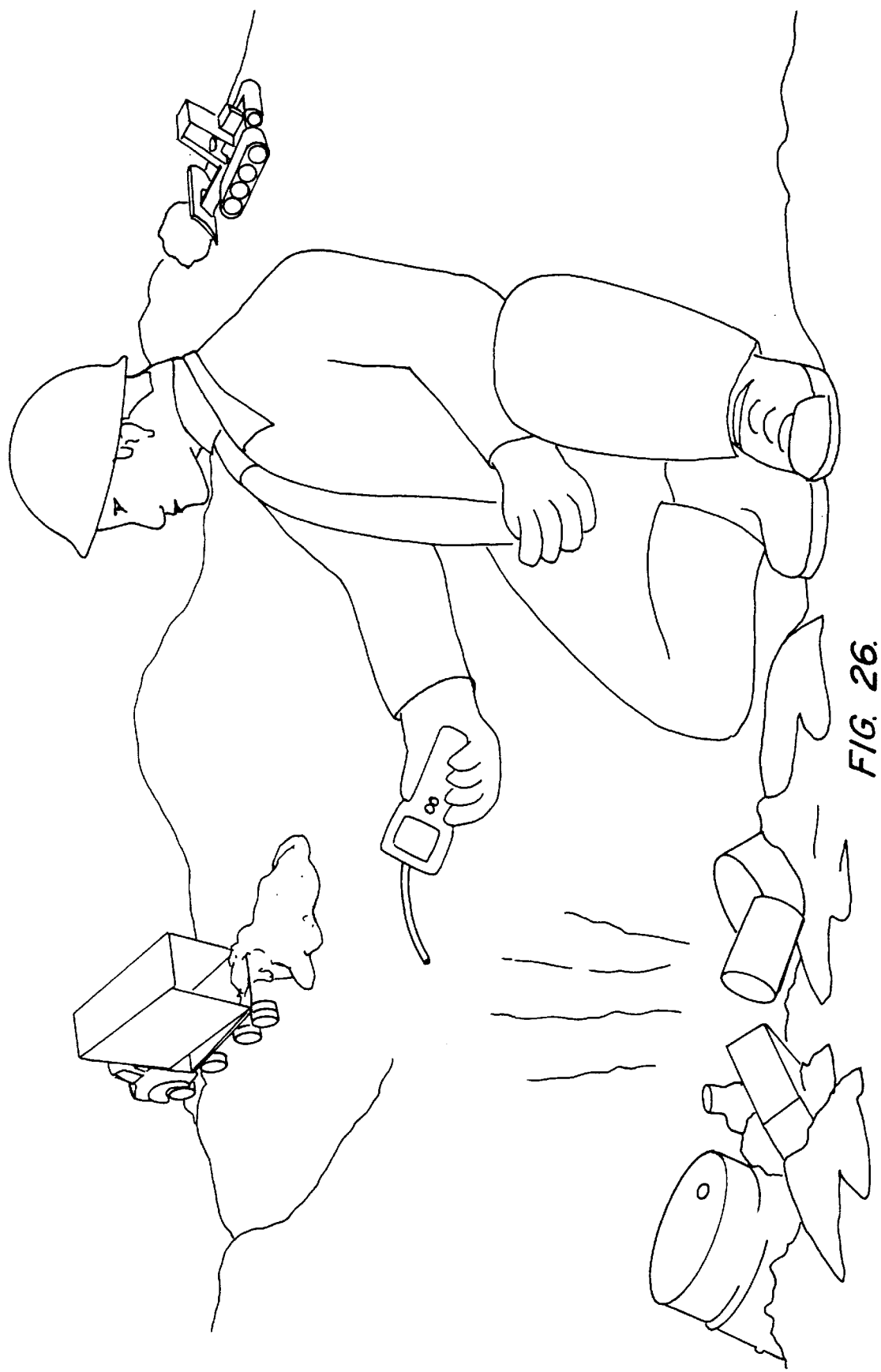
Figure 27:
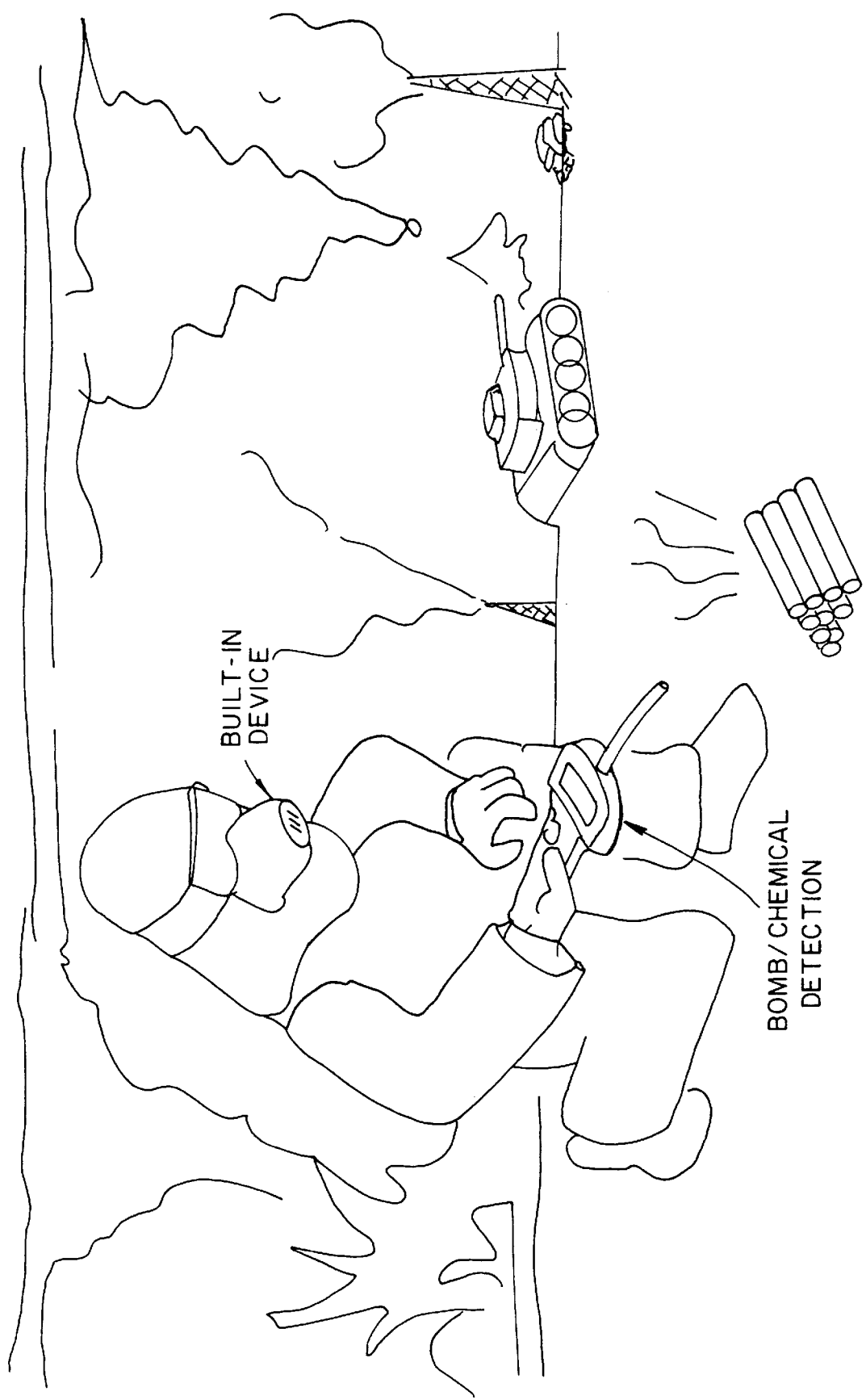
FIG. 27 is a perspective view of a hand held sensor-based fluid detection system used to detect the presence of explosives, e.g., land mines, and other hazardous materials.

Sensor-based detectors (FIGS. 25–27) that determine the presence and/or identity of hazardous materials are useful for fire safety, chemical weapons identification, and for hazardous material teams. The sensors can be tuned to detect noxious poisonous vapors from indoor fires and to warn firefighters or building occupants. Hazmat detectors would find ready use in laboratories for spill detection and in many industrial facilities where chemicals are used. Disposable cartridges may be used to assure the integrity of the unit following each deployment. Bomb squads could use the detectors to identify explosives (e.g., TNT) from a remote sensing position, e.g., employing robotics.

In another embodiment, chemical sensors could be incorporated into chemical warfare protective suit, or hazmat suits, on the inside and/or on the outside, to determine chemical presence, suit leakage, and contamination. These sensor devices can contain neural network software, and the sensor and the electronics can be configured to the needs of each hazmat detection device.

Figure 28:
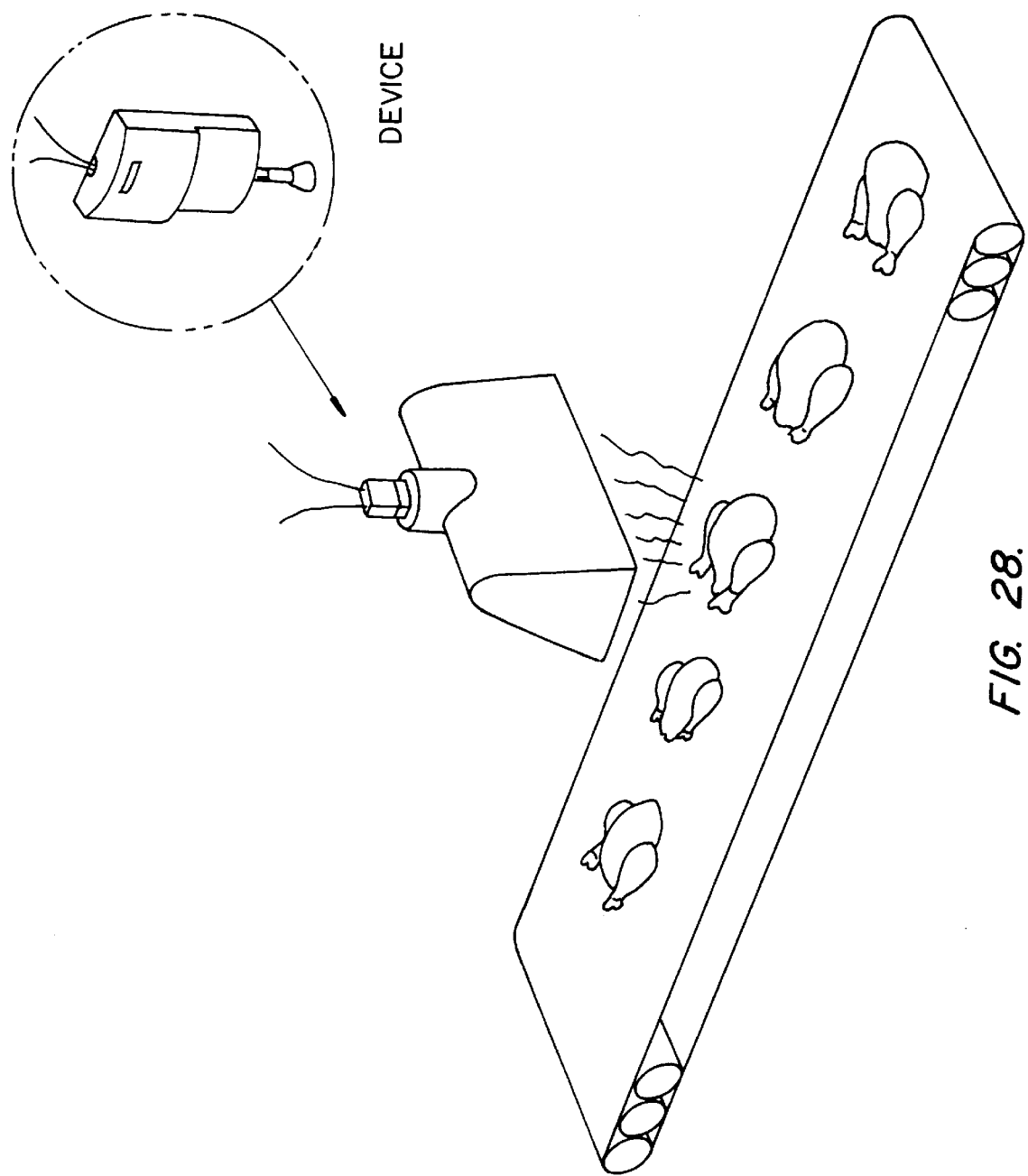
FIG. 28 is a perspective view of a sensor-based fluid detection system used to monitor the condition of food being processed in a food processing plant.
Figure 29:
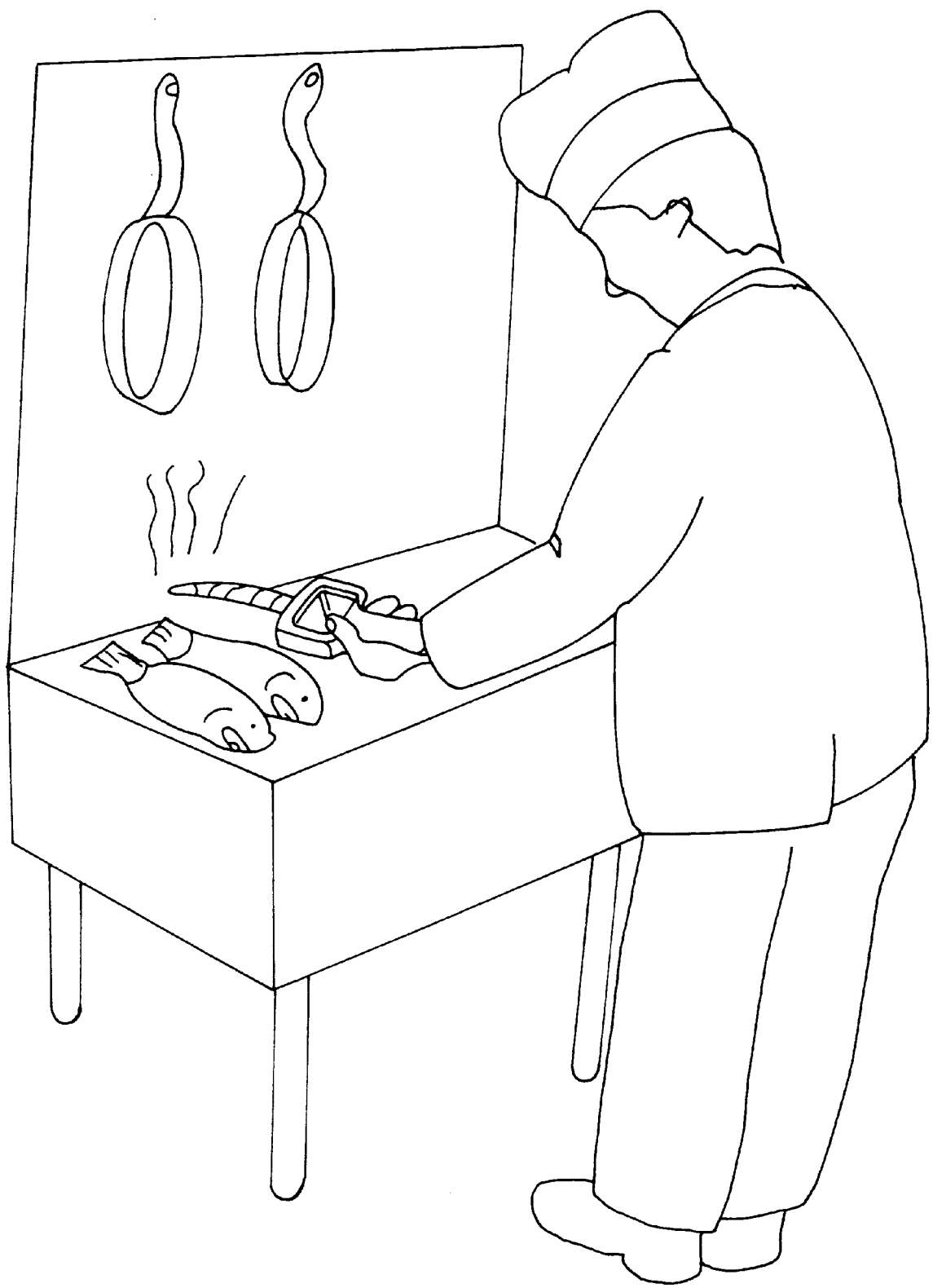
FIG. 29 is a perspective view of a hand held sensor-based fluid detection system used to monitor the condition of food being prepared in a commercial establishment.
Figure 30:
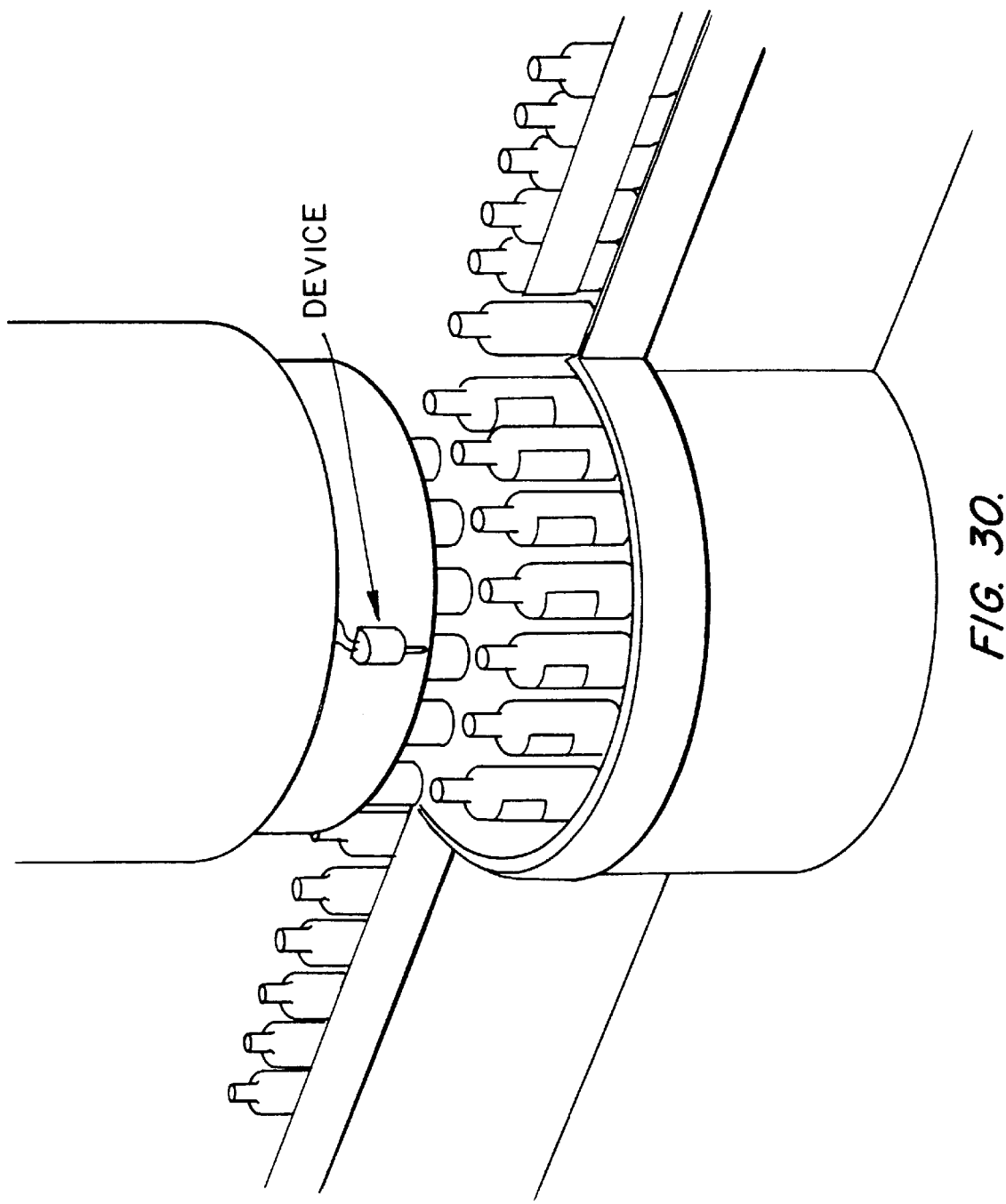
FIG. 30 is a perspective view of a sensor-based fluid detection system used to the monitor the condition of beverages being produced in a bottling plant.

Additional embodiments of the sensor-based fluid detection devices are in the food processing industry (see FIG. 28–30). The sensors can detect spoiled food, or food that does not conform to a specified smell profile. Examples include: *E. coli* in meat; salmonella in chicken; botulinum in canned goods; spoilage of dairy products; fish freshness; etc. The sensor device may be a disposable, sensor-type application or an integrated monitoring device. An example of this embodiment is in the screening of recyclable bottles for contaminants that have residual odors. The sensor devices could also be installed in assembly lines with multiple sensors for mass production applications. Another embodiment is in batch-to-batch consistency of food products. For example, products that are currently tested by either food or beverage tasters and smellers could be monitored with sensor devices to determine whether the particular batch conforms with an ideal response profile. Additionally, any manufacturing processes that can be controlled by odor detection has an applicable sensor device use. Examples include perfume manufacturing, gases for semiconductor fabs, network pipeline feedstocks, and bio-feeds.

Figure 31:
FIG. 31 is a perspective view of a hand held sensor-based fluid detection system used by a law enforcement officer to analyze the breath of a motorist following a motor vehicle accident.

Diagnostic breathalyzer devices for medical and law enforcement uses is another embodiment of the sensor-based fluid detection devices (see FIG. 31). A breathalyzer that differentiates between ethanol and toluene is needed in law enforcement. Toluene poisoning leads to symptoms of ethanol intoxication, but is not illegal. This can cast doubt on the prosecution's evidence, sometimes leading to acquittal. A sensor-based breathalyzer could establish ethanol intoxication beyond a reasonable doubt and assist in prosecuting drunk drivers. The sensor device could have minimum electronics and no neural network, e.g., an ethanol sensor array that simply provides a positive response to ethanol.

Figure 32:
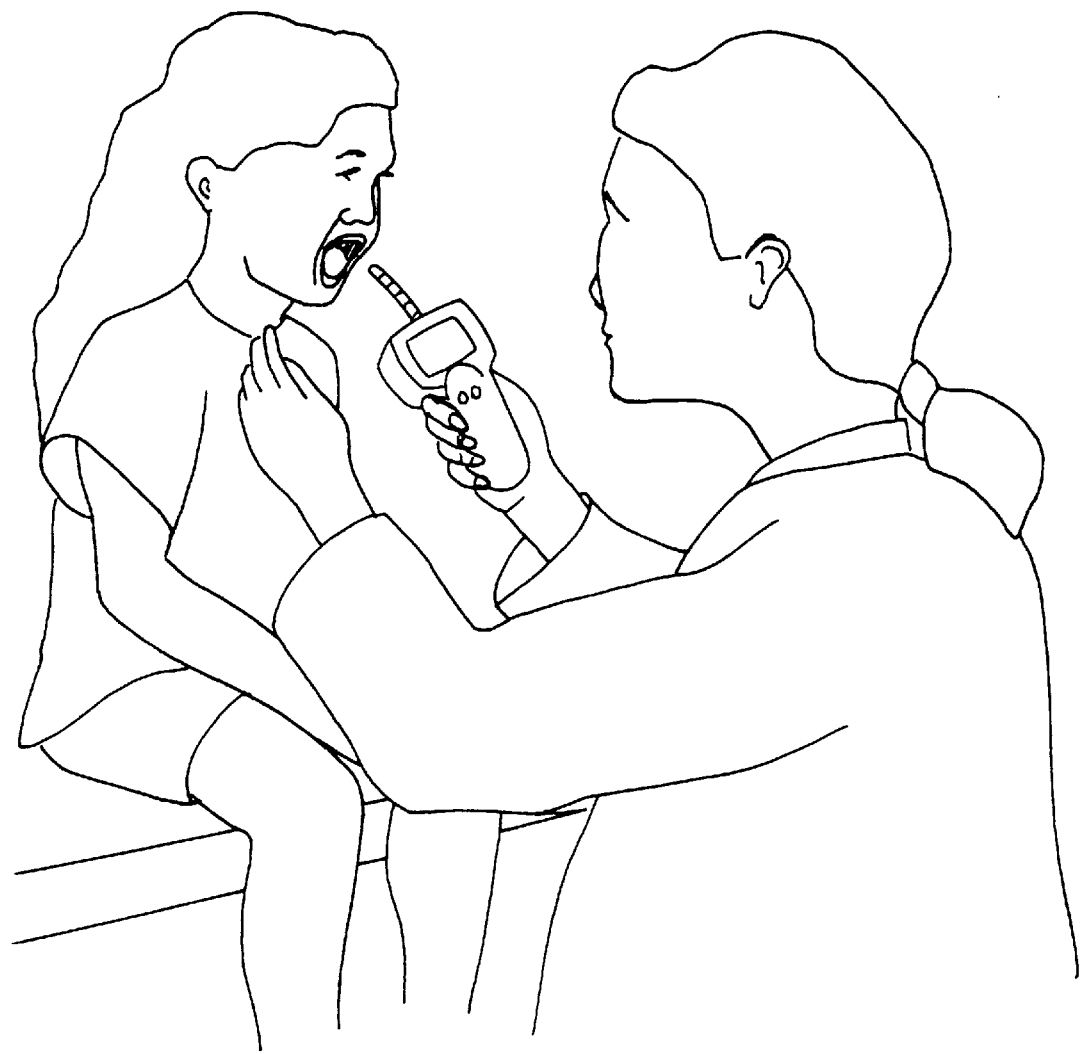
FIG. 32 is a perspective view of a hand held sensor-based fluid detection system used by a medical practitioner to the monitor a patient's breath, as part of a diagnosis of the patient's condition.
Figure 33:
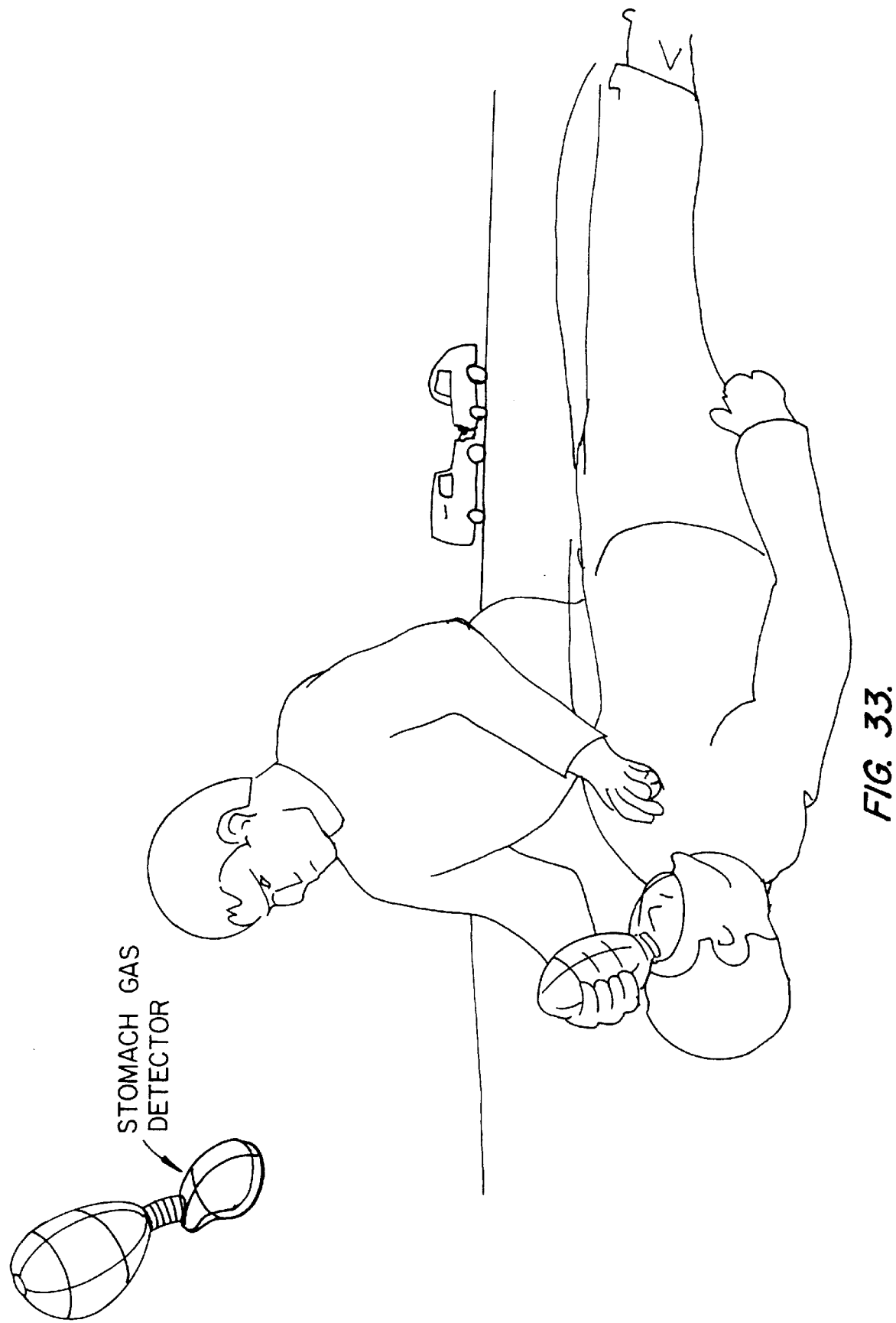
FIG. 33 is a perspective view of a hand held sensor-based fluid detection system used by a emergency medical technician to detect the presence of stomach gas during an intubation procedure.

Medical applications for sensor-based fluid detection involves incorporation into devices for diagnosis and monitoring of patient conditions and diseases (see FIGS. 32–33). The devices would be suitable for doctor's office use, bedside applications, and for acute response medicine, including installation in ambulances. For example, respiratory bacterial infections could be quickly diagnosed from breathalyzer analysis and distinguished from other medical conditions. Other conditions for diagnosis and monitoring using a breathalizer-type apparatus equipped with smell-detecting cartridges or chips keyed for specific applications, include peptic ulcer disease, uremia, ketone levels in diabetes mellitus, exposure to toxic substances, liver disease, and cancers. Bacterial skin conditions are diagnosable using sensor devices and can distinguish bacterial from non-bacterial conditions. Monitoring pre-epileptic and pre-manic states through sweat monitoring, e.g., bracelets or necklaces worn by at-risk individuals is an example of another use. Possible embodiments of the sensor device include portable sensing devices with a fluid delivery appliance, or an integrated disposable sensor device that could be incorporated into bandages.

Figure 34:
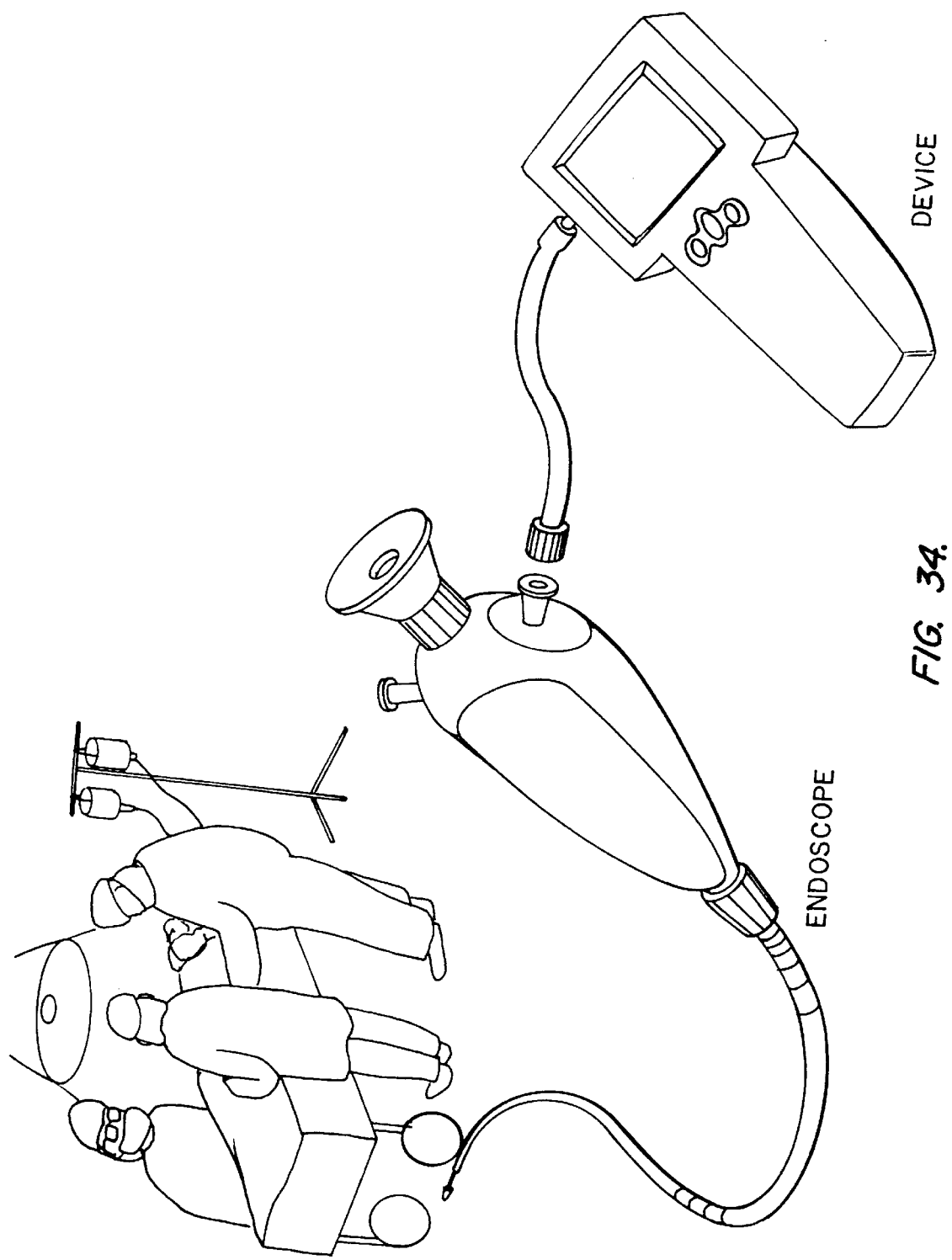
FIG. 34 is a perspective view of a hand held sensor-based fluid detection system integrated into a catheter, for use in monitoring a gases present in certain body cavities.

Chip-based sensors for use in medical diagnostics are an example of another embodiment (See FIG. 34). In a particular embodiment, the sensor device may be integrated into a catheter for examination purposes. This use employs sensor-based probes that may be swallowed, surgically inserted into the body, or inserted into the body through a natural orifice. The sensor device may be coupled with surgical tools, endoscopes, or other surgical devices for diagnosis and consequential medical treatment. Implantable monitors constitute another chip-based embodiment. These implantable monitors can monitor blood gases and alert patients or health care workers when out of specification sensor detection occurs.

The sensor-based fluid detection devices also can be used to detect the presence of ethylene oxide gas. Residual ethylene oxide is a problem in sterilization procedures. In an embodiment of the invention, a sensor-based fluid detection device with a wand could be used to detect the presence of ethylene oxide in sterilized instruments. The sensor device may be a tabletop device or a portable device. In addition, disposable sensor cartridges may be used to detect residual ethylene oxide gas.

The following examples are offered by way of illustration and not by way of limitation.

V. EXAMPLES

Polymer Synthesis. Poly(pyrrole) films used for conductivity, electrochemical, and optical measurements were prepared by injecting equal volumes of $N_2$-purged solutions of pyrrole (1.50 mmoles in 4.0 ml dry tetrahydrofuran) and phosphomolybdic acid (0.75 mmoles in 4.0 ml tetrahydrofuran) into a $N_2$-purged test tube. Once the two solutions were mixed, the yellow phosphomolybdic acid solution turned dark green, with no observable precipitation for several hours. This solution was used for film preparation within an hour of mixing.

Sensor Fabrication. Plasticized poly(pyrrole) sensors were made by mixing two solutions, one of which contained 0.29 mmoles pyrrole in 5.0 ml tetrahydrofuran, with the other containing 0.25 mmoles phosphomolybdic acid and 30 mg of plasticizer in 5.0 ml of tetrahydrofuran. The mixture of these two solutions resulted in a w:w ratio of pyrrole to plasticizer of 2:3. An inexpensive, quick method for crating the chemiresistor array elements was accomplished by effecting a cross sectional cut through commercial 22 nF ceramic capacitors (Kemet Electronics Corporation). Mechanical slices through these capacitors revealed a series of interdigitated metal lines (25% Ag:75% Pt), separated by 15 $\mu$m, that could be readily coated with conducting polymer. The monomer—plasticizer—oxidant solutions were then used to dip coat interdigitated electrodes in order to provide a robust electrical contact to the polymerized organic films. After polymerization was complete, the film was insoluble and was rinsed with solvent (tetrahydrofuran or methanol) to remove residual phosphomolybdic acid and unreacted monomer. The sensors were then connected to a commercial bus strip, with the resistances of the various "chemiresistor" elements readily monitored by use of a multiplexing digital ohmmeter.

Instrumentation. Optical spectra were obtained on a Hewlett Packard 8452A spectrophotometer, interfaced to an IBM XT. Electrochemical experiments were performed using a Princeton Applied Research Inc. 173 potentiostat/175 universal programmer. All electrochemical experiments were performed with a Pt flag auxiliary and a saturated calomel reference electrode (SCE). Spin-coating was performed on a Headway Research Inc. photoresist spin coater. Film thicknesses were determined with a Dektak Model 3030 profilometer. Conductivity measurements were performed with an osmium-tipped four point probe (Alessi Instruments Inc., tip spacing=0.050", tip radii=0.010"). Transient resistance measurements were made with a conventional multimeter (Fluke Inc., "Hydra Data Logger" Meter).

Principle Component Analysis and Multi-linear Least Square Fits. A data set obtained from a single exposure of the array to an odorant produced a set of descriptors (i.e., resistances), $d_i$. The data obtained from multiple exposures thus produced a data matrix D where each row, designated by j, consisted of n descriptors describing a single member of the data set (i.e., a single exposure to an odor). Since the baseline resistance and the relative changes in resistance varied among sensors, the data matrix was autoscaled before further processing [Hecht, *Mathematics in Chemistry: An Introduction to Modern Methods* (Prentice Hall, Englewood Cliffs, N.J.) (1990)]. In this preprocessing technique, all the data associated with a single descriptor (i.e., a column in the data matrix) were centered around zero with unit standard deviation $$d\phi_j = (d_{ij} - \bar{d}\bullet)/p_i \quad (1)$$

where $\bar{d}_i$ is the mean value for descriptor i and ai is the corresponding standard deviation.

Principle component analysis [Hecht, *Mathematics in Chemistry: An Introduction to Modern Methods* (Prentice Hall, Englewood Cliffs, N.J.) (1990)] was performed to determine linear combinations of the data such that the maximum variance [defined as the square of the standard deviation] between the members of the data set was obtained in n mutually orthogonal dimensions. The linear combinations of the data resulted in the largest variance [or separation] between the members of the data set in the first principle component (pc1) and produced decreasing magnitudes of variance from the second to the nth principle component (pc2–pcn). The coefficients required to transform the autoscaled data into principle component space (by linear combination) were determined by multiplying the data matrix, D, by its transpose, $D^T$ (i.e., diagnolizing the matrix) [Hecht, *Mathematics in Chemistry: An Introduction to Modern Methods* (Prentice Hall, Englewood Cliffs, N.J.) (1990)]

$$R = D^T \bullet D \quad (2)$$

This operation produced the correlation matrix, R whose diagonal elements were unity and whose off-diagonal elements were the correlation coefficients of the data. The total variance in the data was thus given by the sum of the diagonal elements in R. The n eigenvalues, and the corresponding n eigenvectors, were then determined for R. Each eigenvector contained a set of n coefficients which were used to transform the data by linear combination into one of its n principle components. The corresponding eigenvalue yielded the fraction of the total variance that was contained in that principle component. This operation produced a principle component matrix, P, which had the same dimensions as the original data matrix. Under these conditions, each row of the matrix P was still associated with a particular odor and each column was associated with a particular principle component.

Since the values in the principle component space had no physical meaning, it was useful to express the results of the principle component analysis in terms of physical parameters such as partial pressure and mole fraction. This was achieved via a multi-linear least square fit between the principle component values and the corresponding parameter of interest. A multi-linear least square fit resulted in a linear combination of the principle components which yielded the best fit to the corresponding parameter value. Fits were achieved by appending a column with each entry being unity to the principle component matrix P, with each row, j, corresponding to a different parameter value (e.g., partial pressure), vj, contained in vector V. The coefficients for the best multi-linear fit between the principle components and parameter of interest were obtained by the following matrix operation $$C = (P^T \bullet P)^{-1} \bullet P^T \bullet V \quad (3)$$

where C was a vector containing the coefficients for the linear combination.

A key to our ability to fabricate chemically diverse sensing elements was the preparation of processable, air stable films of electrically conducting organic polymers. This was achieved through the controlled chemical oxidation of pyrrole (PY) using phosphomolybdic acid $(H_3PMo12O_{40})$ $(_{20}$ in tetrahydrofuran:

$$PY \rightarrow PY^{\bullet+} + e^- \quad (4)$$

$$2PY^{\bullet+} \rightarrow PY_2 + 2H^+ \quad (5)$$

$$H_3PMo_{12}O_{40} + 2e^- + 2H^+ \rightarrow H_5PMo_{12}O_{40} \quad (6)$$

The redox-driven or electrochemically-induced polymerization of pyrrole has been explored previously, but this process typically yields insoluble, intractable deposits of poly(pyrrole) as the product [Salmon et al., *J. Polym. Sci., Polym. Lett.* 20:187–193 (1982)]. Our approach was to use low concentrations of the $H_3PMo_{12}O_{40}$ oxidant ($E°=+0.36$ V vs. SCE) [Pope, *Heteropoly and Isopoly Oxometalates* (Springer-Verlag, New York), chap. 4 (1983)]. Since the electrochemical potential of $PY^+/PY$ is more positive ($E°=+1.30$ V vs. SCE) [Andrieux et al., *J. Am. Chem. Soc.* 112:2439–2440 (1990)] than that of $H_3PMo_{12}O_{40}/H_5PMo_{12}O_{40}$, the equilibrium concentration of $PY^+$, and thus the rate of polymerization, was relatively low in dilute solutions (0.19 M PY, 0.09 M $H_3PMo_{12}O_{40}$). However, it has been shown that the oxidation potential of pyrrole oligomers decreases from +1.20 V to +0.55 to +0.26 V vs. SCE as the number of units increase from one to two to three, and that the oxidation potential of bulk poly(pyrrole) occurs at −0.10 V vs. SCE [Diaz et al., *J. Electroanal. Chem.* 121:355–361 (1981)]. As a result, oxidation of pyrrole trimers by phosphomolybdic acid is expected to be thermodynamically favorable. This allowed processing of the monomer-oxidant solution (i.e., spin coating, dip coating, introduction of plasticizers, etc.), after which time polymerization to form thin films was simply effected by evaporation of the solvent. The dc electrical conductivity of poly(pyrrole) films formed by this method on glass slides, after rinsing the films with methanol to remove excess phosphomolybdic acid and/or monomer, was on the order of 15–30 $S\text{-}cm^{-1}$ for films ranging from 40–100 nm in thickness.

The poly(pyrrole) films produced in this work exhibited excellent electrochemical and optical properties. For example, FIG. 2 shows the cyclic voltammetric behavior of a chemically polymerized poly(pyrrole) film following ten cycles from −1.00 V to +0.70 V vs. SCE. The cathodic wave at −0.40 V corresponded to the reduction of poly(pyrrole) to its neutral, nonconducting state, and the anodic wave at −0.20 V corresponded to the reoxidation of poly(pyrrole) to its conducting state [Kanazawa et al., *Synth. Met.* 4:119–130 (1981)]. The lack of additional faradaic current, which would result from the oxidation and reduction of phosphomolybdic acid in the film, suggests that the Keggin structure of phosphomolybdic acid was not present in the film anions [Bidan et al., *J. Electroanal. Chem.* 251:297–306 (1988)] and implies that $MoO_4^{2-}$, or other anions, served as the poly(pyrrole) counterions in the polymerized films.

FIG. 3A shows the optical spectrum of a processed polypyrrole film that had been spin-coated on glass and then rinsed with methanol. The single absorption maximum was characteristic of a highly oxidized poly(pyrrole) [Kaufinan et al., *Phys. Rev. Lett.* 53:1005–1008 (1984)], and the absorption band at 4.0 eV was characteristic of an interband transition between the conduction and valence bands. The lack of other bands in this energy range was evidence for the presence of bipolaron states (see FIG. 3A), as have been observed in highly oxidized poly(pyrrole) [Kaufman et al., *Phys. Rev. Lett.* 53:1005–1008 (1984)]. By cycling the film in 0.10 M $[(C_4H_9)_4N]^+[ClO_4]^-$—acetonitrile and then recording the optical spectra in 0.10 M KCl—$H_2O$, it was possible to observe optical transitions characteristic of polaron states in oxidized poly(pyrrole) (see FIG. 3B). The polaron states have been reported to produce three optical transitions [Kaufman et al., *Phys. Rev. Lett.* 53:1005–1008 (1984)], which were observed at 2.0, 2.9, and 4.1 eV in FIG. 3B. Upon reduction of the film (c.f. FIG. 3B), an increased intensity and a blue shift in the 2.9 eV band was observed, as expected for the $\pi \rightarrow \pi^*$ transition associated with the pyrrole units contained in the polymer backbone [Yakushi et al., *J. Chem. Phys.* 79:4774–4778 (1983)].

As described in the experimental section, various plasticizers were introduced into the polymer films (Table 3).

TABLE 3

Plasticizers used in array elements*

| sensor | plasticizer |
|---|---|
| 1 | none |
| 2 | none** |
| 3 | poly(styrene) |
| 4 | poly(styrene) |
| 5 | poly(styrene) |
| 6 | poly(a-methyl styrene) |
| 7 | poly(styrene-acrylonitrile) |
| 8 | poly(styrene-maleic anydride) |
| 9 | poly(styrene-allyl alcohol) |
| 10 | poly(vinyl pyrrolidone) |
| 11 | poly(vinyl phenol) |
| 12 | poly(vinyl butral) |
| 13 | poly(vinyl acetate) |
| 14 | poly(carbonate) |

*Sensors contained 2:3 (w:w) ratio of pyrrole to plasticizer.
**Film not rinsed to remove excess phosphomolybdic acid.

These inclusions allowed chemical control over the binding properties and electrical conductivity of the resulting plasticized polymers. Sensor arrays consisted of as many as 14 different elements, with each element synthesized to produce a distinct chemical composition, and thus a distinct sensor response, for its polymer film. The resistance, R, of each film-coated individual sensor was automatically recorded before, during, and after exposure to various odorants. A typical trial consisted of a 60 sec rest period in which the sensors were exposed to flowing air (3.0 liter-$min^{-1}$), a 60 sec exposure to a mixture of air (3.0 liter-$min^{-1}$) and air that had been saturated with solvent (0.5–3.5 liter-$min^{-1}$), and then a 240 sec exposure to air (3.0 liter-$min^{-1}$).

In an initial processing of the data, presented in this paper, the only information used was the maximum amplitude of the resistance change divided by the initial resistance, $\Delta R_{max}/R_i$, of each individual sensor element. Most of the sensors exhibited either increases or decreases in resistance upon exposure to different vapors, as expected from changes in the polymer properties upon exposure to different types chemicals [Topart and Josowicz, *J. Phys. Chem.* 96:7824–7830 (1992); Charlesworth et al., *J. Phys. Chem.* 97:5418–5423 (1993)]. However, in some cases, sensors displayed an initial decrease followed by an increase in resistance in response to a test odor. Since the resistance of each sensor could increase and/or decrease relative to its initial value, two values of $\Delta R_{max}/R_i$ were reported for each sensor. The source of the bi-directional behavior of some sensor/odor pairs has not yet been studied in detail, but in most cases this behavior arose from the presence of water (which by itself induced rapid decreases in the film resistance) in the reagent-grade solvents used to generate the test odors of this study. The observed behavior in response to these air-exposed, water-containing test solvents was reproducible and reversible on a given sensor array, and the environment was representative of many practical odor sensing applications in which air and water would not be readily excluded.

FIGS. 4B–4D depict representative examples of sensor amplitude responses of a sensor array (see, Table 3). In this experiment, data were recorded for three separate exposures to vapors of acetone, benzene, and ethanol flowing in air. The response patterns generated by the sensor array described in Table 3 are displayed for: (B) acetone; (C) benzene; and (D) ethanol. The sensor response was defined as the maximum percent increase and decrease of the resistance divided by the initial resistance (gray bar and black bar, respectively) of each sensor upon exposure to solvent vapor. In many cases sensors exhibited reproducible increases and decreases in resistance. An exposure consisted of: (i) a 60 sec rest period in which the sensors were exposed to flowing air (3.0 liter-min$^{-1}$); (ii) a 60 sec exposure to a mixture of air (3.0 liter-min$^{-1}$) and air that had been saturated with solvent (0.5 liter-min$^{-1}$); and (iii) a 240 sec exposure to air (3.0 liter-min$^{-1}$). It is readily apparent that these odorants each produced a distinctive response on the sensor array. In additional experiments, a total of 8 separate vapors (acetone, benzene, chloroform, ethanol, isopropyl alcohol, methanol, tetrahydrofuran, and ethyl acetate), chosen to span a range of chemical and physical characteristics, were evaluated over a five-day period on a 14-element sensor array (Table 3). As discussed below, each odorant could be clearly and reproducibly identified from the others using this sensor apparatus.

Principle component analysis [Hecht, *Mathematics in Chemistry: An Introduction to Modern Methods* (Prentice Hall, Englewood Cliffs, N.J.) (1990)] was used to simplify presentation of the data and to quantify the distinguishing abilities of individual sensors and of the array as a whole. In this approach, linear combinations of the $\Delta R_{max}/R_i$ data for the elements in the array were constructed such that the maximum variance (defined as the square of the standard deviation) was contained in the fewest mutually orthogonal dimensions. This allowed representation of most of the information contained in data sets shown in FIGS. 4B–4D in two (or three) dimensions. The resulting clustering, or lack thereof, of like exposure data in the new dimensional space was used as a measure of the distinguishing ability, and of the reproducibility, of the sensor array.

Figure 5:
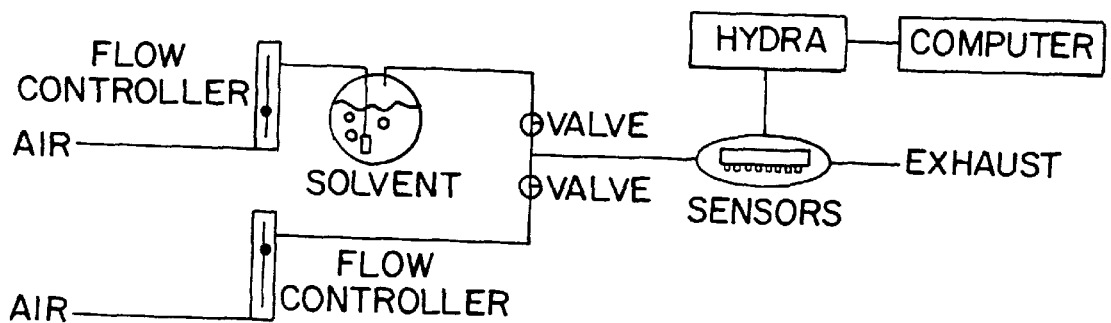
FIG. 5 is a simplified block diagram of the sensor system of the invention.

In order to illustrate the variation in sensor response of individual sensors that resulted from changes in the plasticizing polymer, principle component analysis was performed on the individual, isolated responses of each of the 14 individual sensor elements in a typical array (FIG. 5). Data were obtained from multiple exposures to acetone (a), benzene (b), chloroform (c), ethanol (e), isopropyl alcohol (i), methanol (m), tetrahydrofuran (t), or ethyl acetate (@) over a period of five days with the test vapors exposed to the array in various sequences. The numbers of the figures refer to the sensor elements described in Table 3. The units along the axes indicate the amplitude of the principle component that was used to describe the particular data set for an odor. The black regions indicate clusters corresponding to a single solvent which could be distinguished from all others; gray regions highlight data of solvents whose signals overlapped with others around it. Exposure conditions were identical to those in FIG. 4.

Since each individual sensor produced two data values, principle component analysis of these responses resulted in only two orthogonal principal components; pc1 and pc2. As an example of the selectivity exhibited by an individual sensor element, the sensor designated as number 5 in FIG. 5 (which was plasticized with poly(styrene)) confused acetone with chloroform, isopropyl alcohol, and tetrahydrofuran. It also confused benzene with ethyl acetate, while easily distinguishing ethanol and methanol from all other solvents. Changing the plasticizer to poly (α-methyl styrene) (sensor number 6 in FIG. 5) had little effect on the spatial distribution of the responses with respect to one another and with respect to the origin. Thus, as expected, a rather slight chemical modification of the plasticizer had little effect on the relative variance of the eight test odorants. In contrast, the addition of a cyano group to the plasticizer, in the form of poly(styrene-acrylonitrile), (sensor number 7 in FIG. 5), resulted in a larger contribution to the overall variance by benzene and chloroform, while decreasing the contribution of ethanol. Changing the substituent group in the plasticizer to a hydrogen bonding acid (poly(styrene-allyl alcohol), sensor number 9 in FIG. 5) increased the contribution of acetone to the overall variance while having little effect on the other odors, with the exception of confusing methanol and ethanol. These results suggest that the behavior of the sensors can be systematically altered by varying the chemical composition of the plasticizing polymer.

Figure 6:
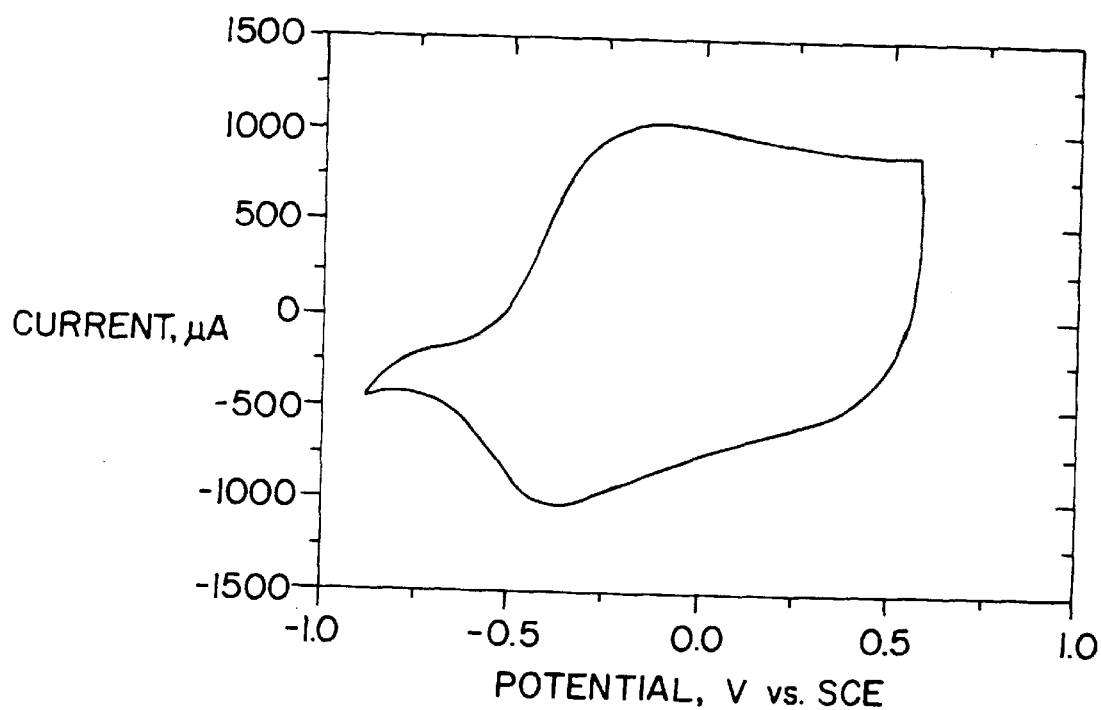
FIG. 6 depicts a cyclic voltammogram of a poly(pyrrole)-coated platinum electrode. The electrolyte was 0.10 M $[(C_4H_9)_4N]^+[ClO_4]^-$ in acetonitrile, with a scan rate of 0.10 V s$^{-1}$.

FIG. 6 shows the principle component analysis for all 14 sensors described in Table 3 and FIGS. 4 and 5. When the solvents were projected into a three dimensional odor space (FIG. 6A or 6B), all eight solvents were easily distinguished with the specific array discussed herein. Detection of an individual test odor, based only on the criterion of observing ~1% $\Delta R_{max}/R_i$ values for all elements in the array, was readily accomplished at the parts per thousand level with no control over the temperature or humidity of the flowing air. Further increases in sensitivity are likely after a thorough utilization of the temporal components of the $\Delta R_{max}/R_i$ data as well as a more complete characterization of the noise in the array.

We have also investigated the suitability of this sensor array for identifying the components of certain test mixtures. This task is greatly simplified if the array exhibits a predictable signal response as the concentration of a given odorant is varied, and if the responses of various individual odors are additive (i.e., if superposition is maintained). When a 19-element sensor array was exposed to a number, n, of different acetone concentrations in air, the $(CH_3)_2CO$ concentration was semi-quantitatively predicted from the first principle component. This was evident from a good linear least square fit through the first three principle components.

Figure 7A:
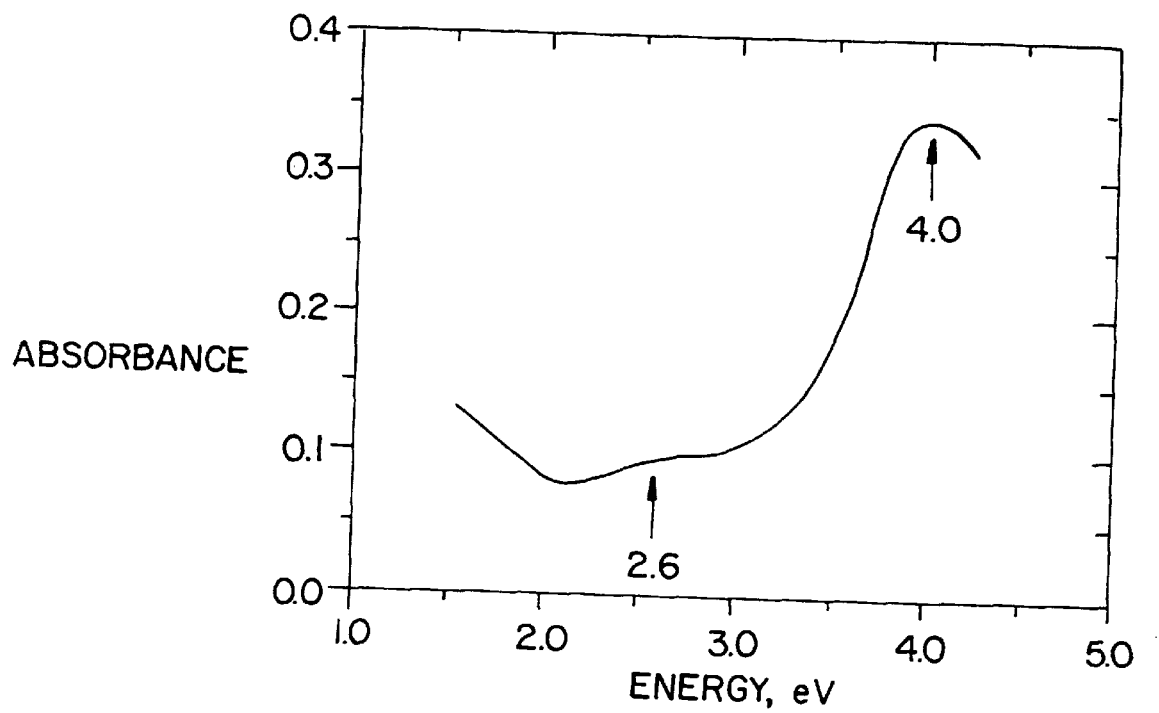
FIG. 7A shows the optical spectrum of a spin coated poly(pyrrole) film that had been washed with methanol to remove excess pyrrole and reduced phosphomolybdic acid.
Figure 7B:
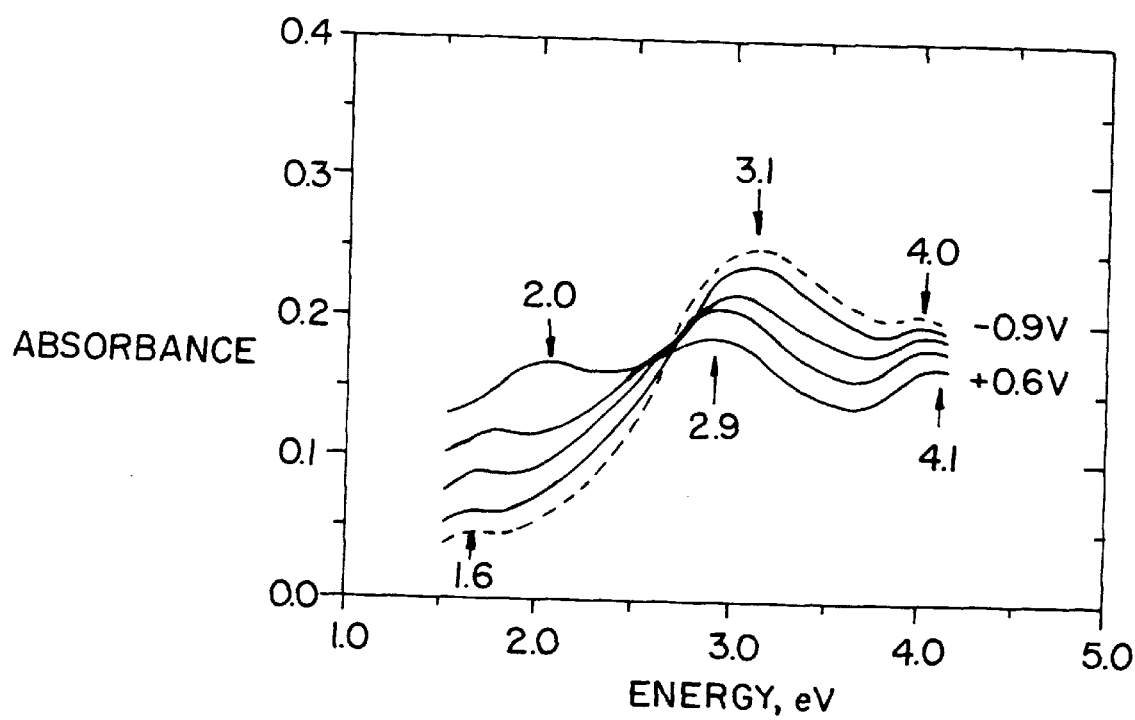
FIG. 7B shows the optical spectrum of a spin-coated poly(pyrrole) film on indium-tin-oxide after ten potential cycles between +0.70 and −1.00 V vs. SCE in 0.10 M $[(C_4H_9)_4N]^+[ClO_4]^-$— in acetonitrile at a scan rate of 0.10 V $\cdot s^{-1}$. The spectra were obtained in 0.10 M KCl—$H_2O$.

The same sensor array was also able to resolve the components in various test methanol-ethanol mixtures. As shown in FIG. 7B, a linear relationship was observed between the first principle component and the mole fraction of methanol in the liquid phase, $x_m$, in a $CH_3OH-C_2H_5OH$ mixture, demonstrating that superposition held for this mixture/sensor array combination. Furthermore, although the components in the mixture could be predicted fairly accurately from just the first principle component, an increase in the accuracy could be achieved using a multi-linear least square fit through the first three principle components. This relationship held for $CH_3OH/(CH_3OH+C_2H_5OH)$ ratios of 0 to 1.0 in air-saturated solutions of this vapor mixture. The conducting polymer-based sensor arrays could therefore not only distinguish between pure test vapors, but also allowed analysis of concentrations of odorants as well as analysis of binary mixtures of vapors.

In summary, the results presented herein advance the area of analyte sensor design. A relatively simple array design, using only a multiplexed low-power dc electrical resistance readout signal, has been shown to readily distinguish between various test odorants. Such conducting polymer-based arrays are simple to construct and modify, and afford an opportunity to effect chemical control over the response pattern of a vapor. For example, by increasing the ratio of plasticizer to conducting polymer, it is possible to approach the percolation threshold, at which point the conductivity exhibits a very sensitive response to the presence of the sorbed molecules. Furthermore, producing thinner films will afford the opportunity to obtain decreased response times, and increasing the number of plasticizing polymers and polymer backbone motifs will likely result in increased diversity among sensors. This type of polymer-based array is chemically flexible, is simple to fabricate, modify, and analyze, and utilizes a low power dc resistance readout signal transduction path to convert chemical data into electrical signals. It provides a new approach to broadly-responsive odor sensors for fundamental and applied investigations of chemical mimics for the mammalian sense of smell. Such systems are useful for evaluating the generality of neural network algorithms developed to understand how the mammalian olfactory system identifies the directionality, concentration, and identity of various odors.

Fabrication and Testing of Carbon Black-based Sensor Arrays.

Sensor Fabrication. Individual sensor elements were fabricated in the following manner. Each non-conductive polymer (80 mg, see Table 4) was dissolved in 6 ml of THF.

TABLE 4

| Sensor # | Non-Conductive Polymer |
|---|---|
| 1 | poly(4-vinyl phenol) |
| 2 | poly(styrene - allyl alcohol) |
| 3 | poly($\alpha$-methyl styrene) |
| 4 | poly(vinyl chloride - vinyl acetate.) |
| 5 | poly(vinyl acetate) |
| 6 | poly(N-vinyl pyrrolidone) |
| 7 | poly(bisphenol A carbonate) |
| 8 | poly(styrene) |
| 9 | poly(styrene-maleic anhydride) |
| 10 | poly(sulfone) |

Then, 20 mg of carbon black (BP 2000, Cabot Corp.) were suspended with vigorous mixing. Interdigitated electrodes (the cleaved capacitors previously described) were then dipped into this mixture and the solvent allowed to evaporate. A series of such sensor elements with differing non-conductive polymers were fabricated and incorporated into a commercial bus strip which allowed the chemiresistors to be easily monitored with a multiplexing ohmmeter.

Figure 9:
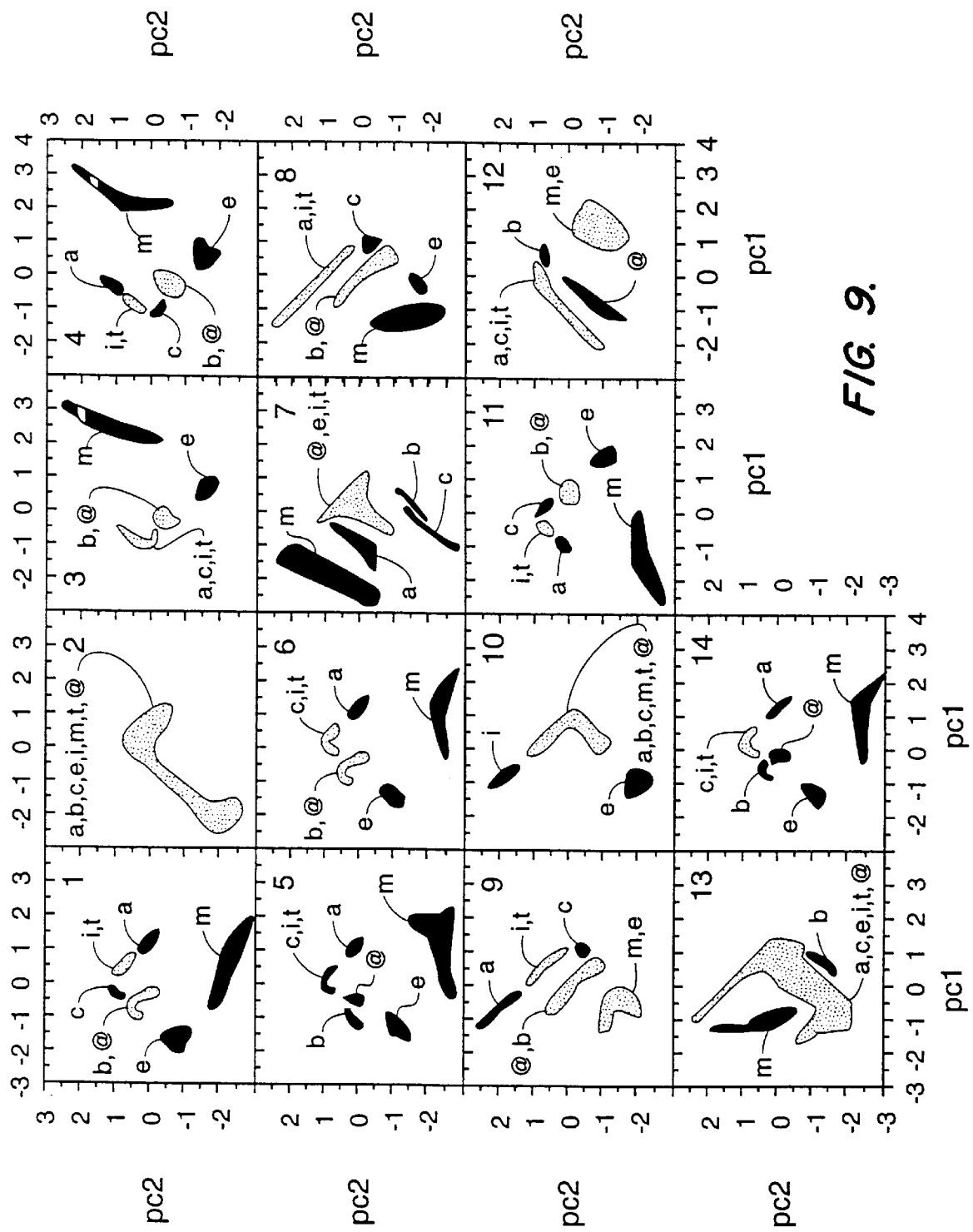
FIGS. 9A–D schematically depicts a principle component analysis of autoscaled data from individual sensors containing different plasticizers. The numbers in the upper right corner of each depicted square refer to the different sensor elements described in Table 3.
Figure 10A:
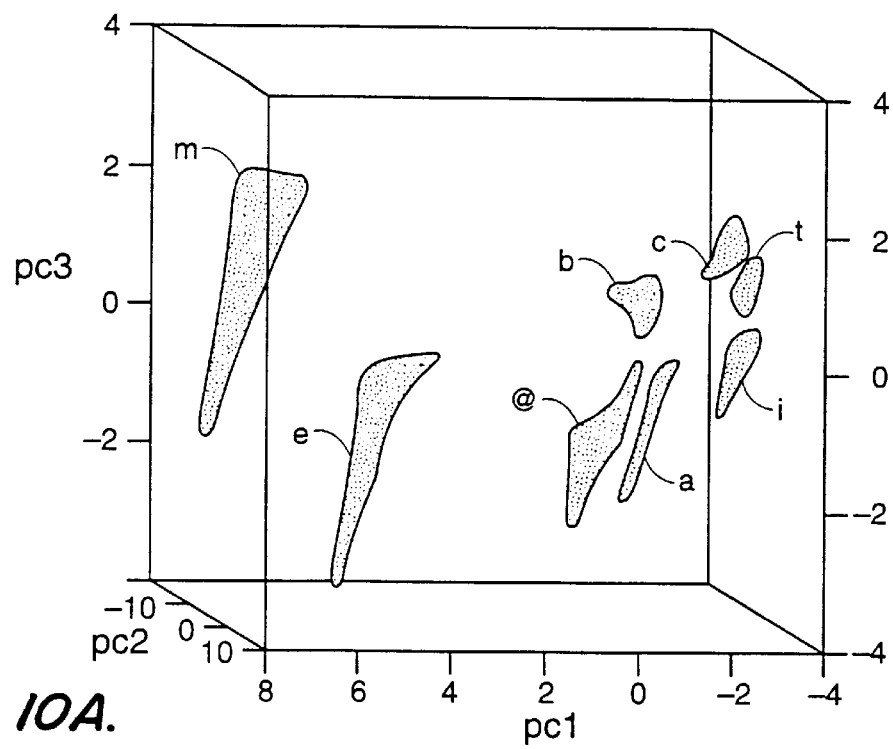
FIGS. 10A–B depict a principle component analysis of data obtained from all of the sensors of Table 3. Conditions and symbols are identical to FIGS. 9A–D.
Figure 10B:
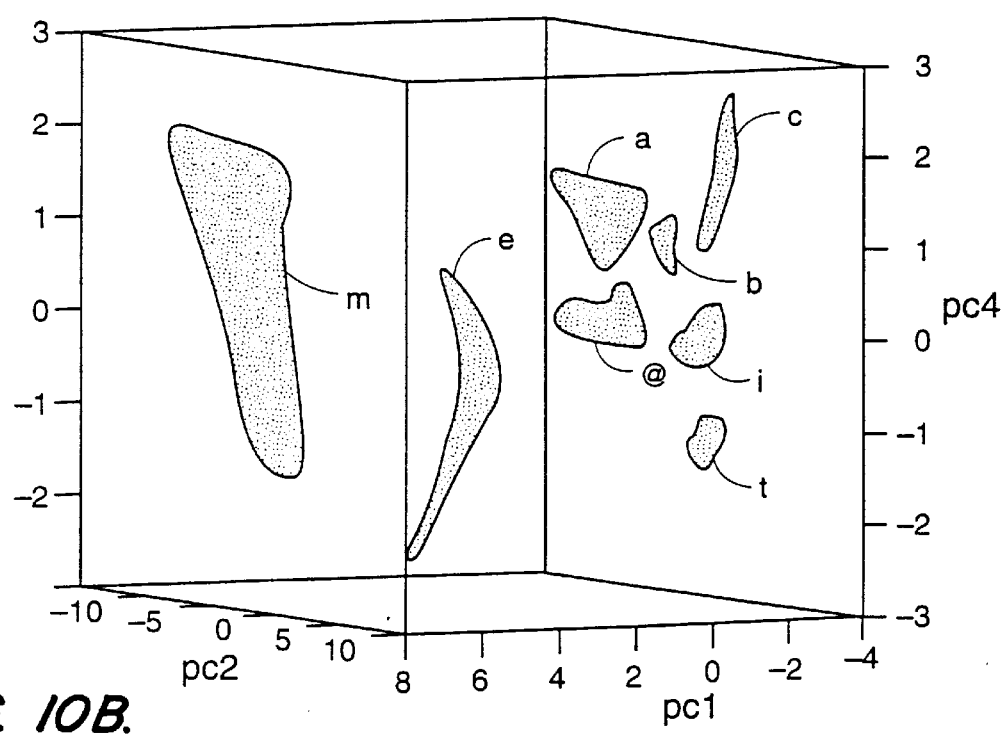
Figure 11A:
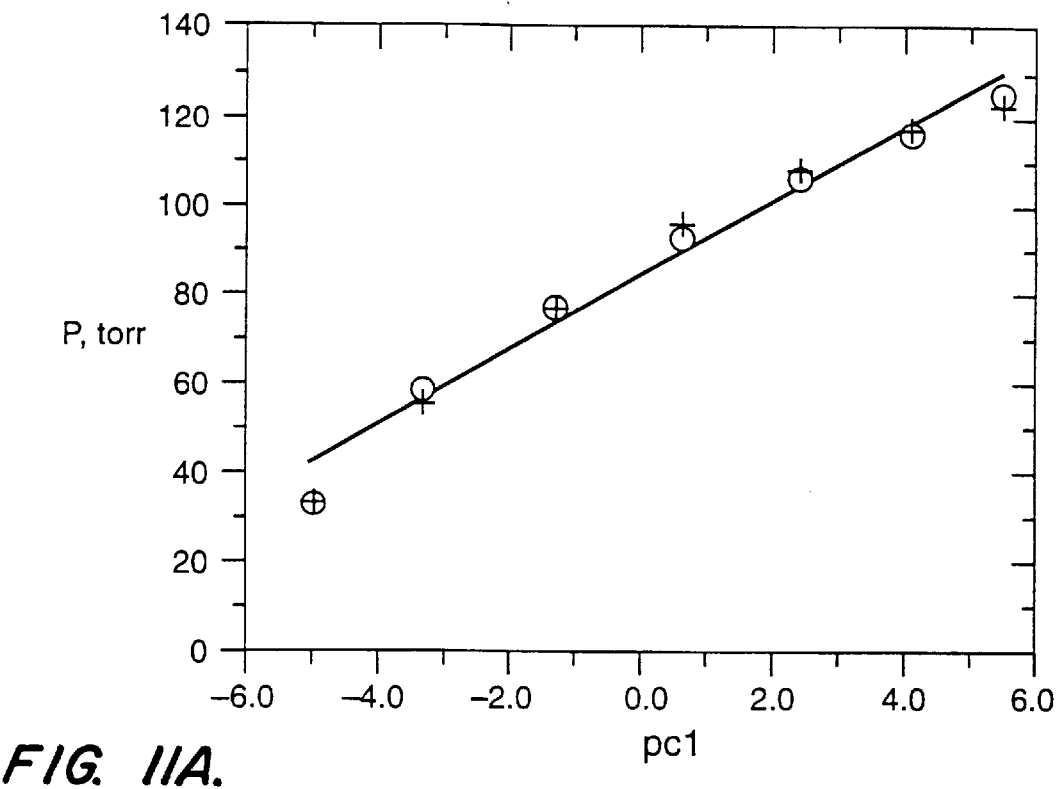
FIG. 11A is a plot of acetone partial pressure (O) as a function of the first principle component; linear least square fit (—) between the partial pressure of acetone and the first principle component ($P_a$=8.26·pc1+83.4, $R_2$=0.989); acetone partial pressure (+) predicted from a multi-linear least square fit between the partial pressure of acetone and the first three principle components ($P_a$=8.26·pc1−0.673·pc2+6.25·pc3+83.4, $R^2$=0.998).
Figure 11B:
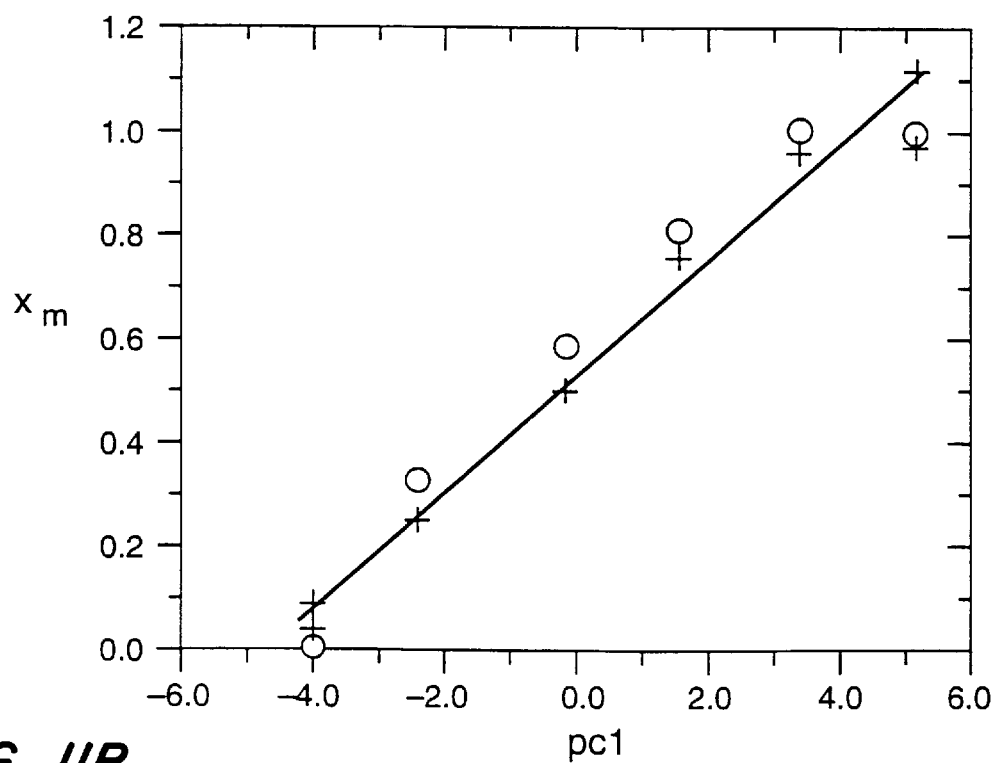
FIG. 11B is a plot of the mole fraction of methanol, $x_m$, (O) in a methanol-ethanol mixture as a function of the first principle component; linear least square fit (—) between $x_m$ and the first principle component ($x_m$=0.112·pc1+0.524, $R^2$=0.979); $x_m$ predicted from a multi-linear least square fit (+) between $x_m$ and the first three principle components ($x_m$=0.112·pc1−0.0300·pc2−0.0444·pc3+0.524, $R^2$=0.987).
Figure 12:
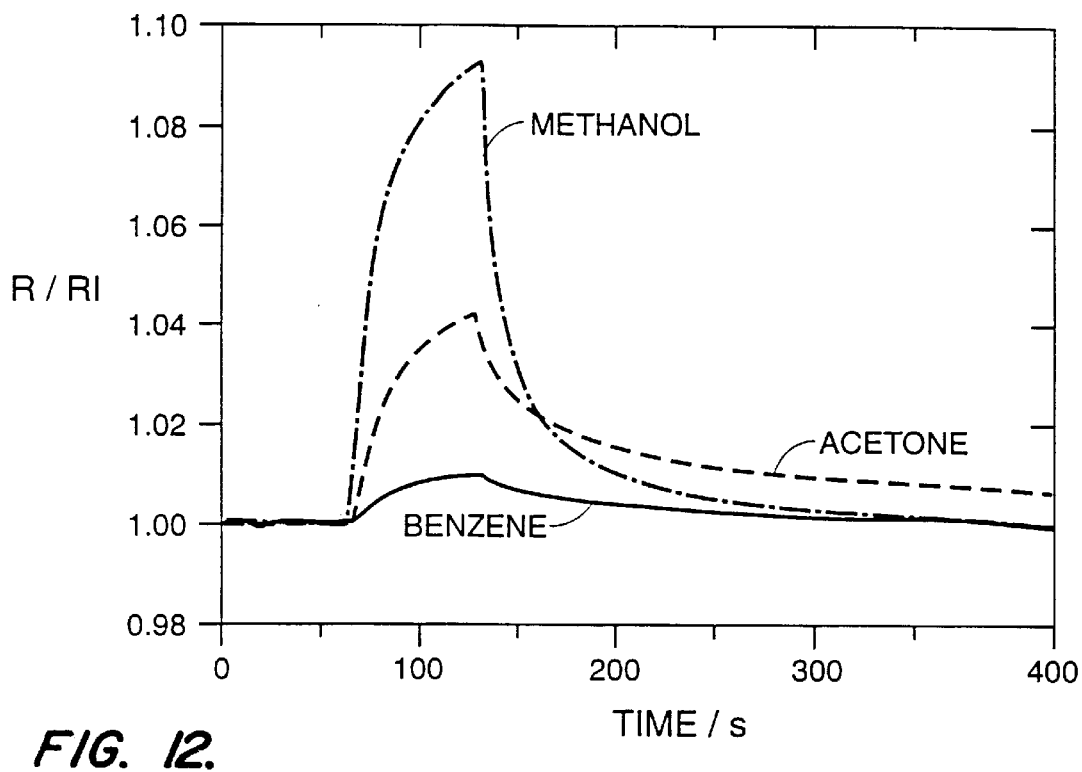
FIG. 12 is a plot of the resistance response of a poly(N-vinylpyrrolidone):carbon black (20 w/w % carbon black) sensor element to methanol, acetone, and benzene. The analyte was introduced at t=60 s for 60 s. Each trace is normalized by the resistance of the sensor element (approx. 125 ohms) before each exposure.
Figure 13:
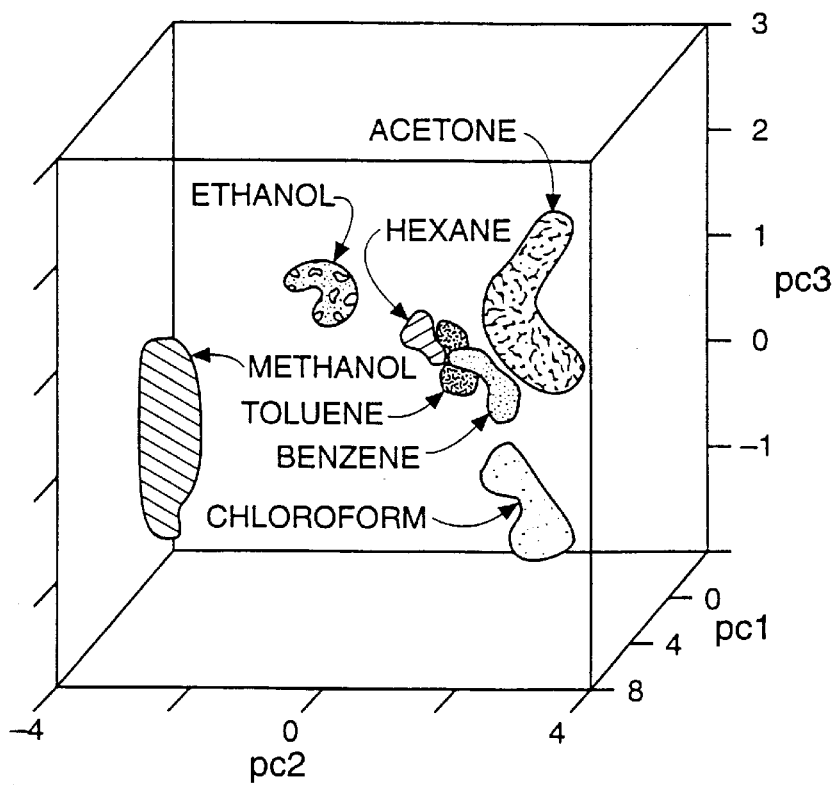
FIG. 13 is a schematic representation of the first three principal components for the response of a carbon-black based sensor array with ten elements. The non-conductive components of the carbon-black composites used are listed in Table 3, and the resistors were 20 w/w % carbon black.

Sensor Array Testing. To evaluate the performance of the carbon-black based sensors, arrays with as many as 20 elements were exposed to a series of analytes. A sensor exposure consisted of (1) a 60 second exposure to flowing air (6 liter min-1, (2) a 60 second exposure to a mixture of air (6 liter min-1) and air that had been saturated with the analyte (0.5 liter min-1), (3) a five minute recovery period during which the sensor array was exposed to flowing air (6 liter min-1). The resistance of the elements were monitored during exposure, and depending on the thickness and chemical make-up of the film, resistance changes as large as 250% could be observed in response to an analyte. In one experiment, a 10 element sensor array consisting carbon-black composites formed with a series of non-conductive polymers (see Table 4) was exposed to acetone, benzene, chloroform, ethanol, hexane, methanol, and toluene over a two day period. A total of 58 exposures to these analytes were performed in this time period. In all cases, resistance changes in response to the analytes were positive, and with the exception of acetone, reversible (see FIG. 8). The maximum positive deviations were then subjected to principal component analysis in a manner analogous to that described for the poly(pyrrole) based sensor. FIG. 9 shows the results of the principal component analysis for the entire 10-element array. With the exception of overlap between toluene with benzene, the analytes were distinguished from one and other.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining the presence of an analyte, said method comprising:

providing an integrated system comprising a sensor assembly that includes a plurality of compositionally different sensors wherein each sensor comprises a matrix of alternating nonconductive organic regions and conductive regions, and provides a response to the presence of vapor in contact therewith;

measuring the response to said vapor using a detector; and comparing the measured response with a stored response to determine the presence of said analyte.

2. The method according to claim 1, wherein said analyte is indicative of diagnosing and monitoring a patient condition and disease.

3. The method according to claim 2, wherein said analyte is indicative of a member selected from the group consisting of a peptic ulcer disease, uremia, ketone levels in diabetes mellitus, exposure to a toxic substance, liver disease, and cancer.

4. The method according to claim 1, wherein said analyte is indicative of a bacterial skin condition.

5. The method according to claim 1, wherein said analyte is in blood.

6. The method according to claim 1, wherein said sensor is incorporated into bandages.

7. The method according to claim 1, wherein said sensor is disposable.

8. The method according to claim 1, wherein said analyte is indicative of spoiled food.

9. The method according to claim 1, wherein said analyte is indicative of *E. coli*.

10. The method according to claim 1, wherein said analyte is indicative of salmonella.

11. The method according to claim 1, wherein said analyte is indicative of botulinum.

12. The method according to claim 1, wherein said analyte is indicative of spoilage of a dairy product.

13. The method according to claim 1, wherein said analyte is indicative of fish freshness.

14. The method according to claim 1, wherein said analyte is indicative of quality control in a beverage product.

15. The method according to claim 1, wherein said analyte is indicative of ethanol intoxication.

16. The method according to claim 1, wherein said analyte is indicative of quality control in a food product.

17. The method according to claim 1, wherein said analyte is indicative of food cooking and heating processes.

18. The method according to claim 1, wherein said analyte is indicative of environment air quality.

19. The method according to claim 1, wherein said analyte is indicative of noxious poisonous vapors.

\* \* \* \* \*

UNITED STATES PATENT AND TRADEMARK OFFICE
CERTIFICATE OF CORRECTION

PATENT NO.    : 6,170,318 B1
DATED         : January 9, 2001
INVENTOR(S)   : Lewis It is certified that error appears in the above-identified patent and that said Letters Patent is hereby corrected as shown below:

Column 28,
Line 17, before "matrix", please add -- sensing --.
Line 18, please delete "and provides", and replace with -- that provides --.

Signed and Sealed this

Seventeenth Day of December, 2002

JAMES E. ROGAN
*Director of the United States Patent and Trademark Office*